United States Patent
Kheifets et al.

(10) Patent No.: US 11,660,316 B2
(45) Date of Patent: May 30, 2023

(54) METHODS OF INDUCING LIVER REGENERATION BY ADMINISTERING A PLASMA PROTEIN FRACTION

(71) Applicant: Alkahest, Inc., San Carlos, CA (US)

(72) Inventors: Viktoria Kheifets, Mountain View, CA (US); Benson Lu, San Francisco, CA (US)

(73) Assignee: Alkahest, Inc., San Carlos, CA (US)

( * ) Notice: Subject to any disclaimer, the term of this patent is extended or adjusted under 35 U.S.C. 154(b) by 123 days.

(21) Appl. No.: 16/951,891

(22) Filed: Nov. 18, 2020

(65) Prior Publication Data

US 2021/0145875 A1 May 20, 2021

Related U.S. Application Data

(60) Provisional application No. 62/975,637, filed on Feb. 12, 2020, provisional application No. 62/937,965, filed on Nov. 20, 2019.

(51) Int. Cl.
| | | |
|---|---|---|
| *A61K 35/16* | (2015.01) | |
| *A61P 1/16* | (2006.01) | |
| *A61K 38/38* | (2006.01) | |
| *A61K 38/17* | (2006.01) | |

(52) U.S. Cl.
CPC .......... *A61K 35/16* (2013.01); *A61K 38/1722* (2013.01); *A61K 38/38* (2013.01); *A61P 1/16* (2018.01)

(58) Field of Classification Search
CPC .... A61K 35/16; A61K 38/1722; A61K 38/38; A61P 1/16
See application file for complete search history.

(56) References Cited

U.S. PATENT DOCUMENTS

| | | |
|---|---|---|
| 10,245,285 B2 | 4/2019 | Braithwaite et al. |
| 10,357,513 B2 | 7/2019 | Braithwaite et al. |
| 10,525,107 B2 | 1/2020 | Bell et al. |
| 10,688,130 B2 | 6/2020 | Wyss-Coray et al. |
| 10,874,692 B2 | 12/2020 | Braithwaite et al. |
| 10,905,717 B2 | 2/2021 | Braithwaite et al. |
| 10,905,779 B2 | 2/2021 | Braithwaite et al. |
| 11,103,530 B2 | 8/2021 | Castro et al. |
| 11,298,377 B2 | 4/2022 | Kheifets et al. |
| 2003/0036638 A1* | 2/2003 | Joergensen ............ C07K 14/47 530/417 |
| 2011/0201548 A1 | 8/2011 | Sasaki et al. |
| 2012/0171206 A1 | 7/2012 | Tomlinson et al. |
| 2015/0157664 A1 | 6/2015 | Wyss-Coray et al. |
| 2017/0232118 A1 | 8/2017 | Braithwaite et al. |
| 2017/0340671 A1 | 11/2017 | Braithwaite et al. |
| 2018/0110839 A1 | 4/2018 | Bell et al. |
| 2018/0250368 A1* | 9/2018 | Bataille ................ A61P 3/00 |
| 2018/0282368 A1 | 10/2018 | Zhang et al. |
| 2018/0311280 A1 | 11/2018 | Braithwaite et al. |
| 2019/0167719 A1 | 6/2019 | Braithwaite et al. |
| 2019/0282617 A1 | 9/2019 | Braithwaite et al. |
| 2019/0298800 A1 | 10/2019 | Dasseux et al. |
| 2019/0321449 A1 | 10/2019 | Bell et al. |
| 2019/0328782 A1 | 10/2019 | Braithwaite et al. |
| 2020/0129549 A1 | 4/2020 | Castro et al. |
| 2020/0352994 A1 | 11/2020 | Wyss-Coray et al. |
| 2021/0113612 A1 | 4/2021 | Braithwaite et al. |
| 2021/0128693 A1 | 5/2021 | Kheifets et al. |
| 2021/0268021 A1* | 9/2021 | Kheifets ................ A61P 1/16 |

FOREIGN PATENT DOCUMENTS

| | | |
|---|---|---|
| JP | 2000-106882 A | 4/2000 |
| WO | WO2006116380 A2 | 11/2006 |
| WO | WO2007139291 A1 | 12/2007 |
| WO | WO2015088915 A1 | 6/2015 |
| WO | WO2017189919 A1 | 11/2017 |
| WO | WO-2017189919 A2 * | 11/2017 ............. A61K 35/16 |
| WO | WO2018034712 A1 | 2/2018 |
| WO | WO2018200560 A1 | 11/2018 |
| WO | WO2020018343 A1 | 1/2020 |
| WO | WO2020086469 A1 | 4/2020 |

OTHER PUBLICATIONS

Conboy et al., Rejuvenation of aged progenitor cells by exposure to a young systemic environment, Nature. Feb. 17, 2005;433(7027):760-4.

Rebo et al., A single heterochronic blood exchange reveals rapid inhibition of multiple tissues by old blood, Nat Commun. Nov. 22, 2016;7:13363.

Strengers, Evidence-based clinical indications of plasma products and future prospects, Ann Blood, Dec. 2017;2:20.

\* cited by examiner

*Primary Examiner* — Aaron J Kosar
(74) *Attorney, Agent, or Firm* — Mandar A. Joshi; Bret E. Field; Bozicevic, Field & Francis LLP

(57) ABSTRACT

Provided herein are methods of inducing liver regeneration in a subject diagnosed with a liver disorder. The method comprises administering a Plasma Protein Fraction (PPF) to the subject. In certain embodiments, the PPF comprises between 83% and 95% albumin in relation to total proteins. The PPF can be produced from plasma obtained from young individuals, for example, humans 40 years of age or younger.

8 Claims, 34 Drawing Sheets

Resected

Resected

Remnant

Remnant

Post-Hepatectomy

Remnant

Remnant

Remnant

Resected

Resected

Resected

Resected

Resected

Resected

Figure 17

| Total | Pre-Hepatectomy | Post-Hepatectomy | % Survival |
|---|---|---|---|
| Total Animals | 28 | 22 | 78.57 |
| PPF1 | 15 | 13 | 86.67 |
| Vehicle | 13 | 10 | 76.92 |

Stellate

Kupffer

Hepatocyte

T-cells

Liver Sinusoidal Endothelial Cells (LSECs)

METHODS OF INDUCING LIVER REGENERATION BY ADMINISTERING A PLASMA PROTEIN FRACTION

I. BACKGROUND

This invention pertains to the prevention and treatment of disease including aging-associated disease. The invention relates to the use of blood products, such as blood plasma and blood plasma fractions to treat and/or prevent conditions associated with aging associated with liver growth, maintenance, and regeneration. Pursuant to 35 U.S.C. § 119(e), this application claims priority to the filing dates of U.S. Provisional Patent Application Ser. No. 62/937,965 filed Nov. 20, 2019; and U.S. Provisional Patent Application Ser. No. 62/975,637 filed Feb. 12, 2020; the disclosures of which applications are incorporated herein by reference.

II. SUMMARY

Liver failure is a large market with currently a single therapeutic intervention—liver transplantation. One out of 10 Americans, about 35 million people, have some form of liver disease. This number is increasing due to the prevalence of cirrhotic liver disease of an increasingly obese population. NAFLD (non-alcoholic fatty liver disease) is a major risk factor that contributes to liver cirrhosis which can lead to eventual liver failure. The available organs for transplantation are low due to decreased health of the general population. As a result, only about ⅓ of the patients on the liver transplant list receive a transplant. The list generally excludes patients over 65 years of age due to age-related increases in risks associated with organ transplantation. For the cirrhotic patients awaiting liver transplantation the statistics are especially dire. There are 300,000 cirrhosis-based hospitalizations, 36,000 cirrhosis deaths per year in the US and more than half of these patients are not eligible for transplantation. Availability of an alternative therapeutic approach could significantly impact a large segment of liver disease patients who would otherwise have no available treatment.

Liver failure can be acute or chronic. Acute liver failure is often caused by viral infections (e.g. Hepatitis B and C), overuse of drugs or toxins (e.g. acetaminophen), and metabolic or vascular disorders like autoimmune hepatitis and Wilson disease. Chronic liver failure is usually categorized as cirrhosis and can be caused by viral infections, alcohol abuse, NAFLD (caused by obesity, high cholesterol and triglycerides, and high blood pressure), autoimmune disorders, blocked or damaged tubes such as bile ducts from the liver to the intestine, exposure to toxins or certain medicines, parasites, heart failure resulting in buildup of blood in the liver.

Liver resection and transplantation may be performed for liver failure as described above, with transplantation more generally performed with chronic liver failure. Additionally, these procedures can be performed for primary and secondary malignancies (i.e. cancers). Improved outcomes of liver resection and transplantation have been associated with attention to pre, peri, and post-operative care. (Wrighton L J, et al., *J Gastrointest Oncol.*, 3(1): 41-47, (2012)). These include advances in surgical and anesthetic techniques, an improved understanding of hepatic physiology, nutritional support, glycemic control, and reduction of post-operative infections. (Id.) In the case of liver transplants, immunosuppressants are most commonly used. The role of the primary physician in managing liver rejection as well as care for long-term complications such as hypertension and obesity has been an important part of improving outcomes. (See, Issa D H, *Cleveland Clinic J of Med.*, 82(6):361-72 (2015)).

There is still a significant lack of new therapies to improve outcome of those suffering from liver failure and/or undergoing resection or transplants. Further, even in the case of liver transplant surgery, there simply are not enough donor livers for all patients. (See, e.g., Helwick C, *The ASCO Post*, (Sep. 25, 2017) stating that the "problem with transplantation is organ allocation.")

One compound being studied for treatment of liver cirrhosis is albumin. This is in order to replace lost albumin production due to decreased production of albumin by the cirrhotic liver itself. The rationale has been that albumin helps in replacement of osmotic pressure, binding toxic substances, modulation of homeostasis, and acting as an anti-inflammatory. (Carvalho J R, et al., *Annals of Hepatology*, 17(4): 547-60 (2018)). Thus, conventional thought in the field is that the purer the albumin, the higher the concentration resulting in more efficacy. Therapeutic albumin is commonly produced through blood plasma fractionation. Fractionation can produce albumin solutions albeit with unwanted protein "contaminants" or "impurities."

The present invention provides new therapies using fractions of blood plasma to improve and accelerate recovery of diseased, resected, or transplanted livers in patients suffering from liver disease. Additionally, since the liver is the only visceral organ capable of regeneration, the present invention provides methods to stimulate proliferation and regeneration in existing liver, which in some liver-associated indications can, for example, facilitate recovery from surgeries. Further, the present invention makes use of what has been considered "contaminants" or "impurities" derived from plasma fractionation to more effectively treat liver disease.

III. INCORPORATION BY REFERENCE

All publications and patent applications mentioned in this specification are herein incorporated by reference to the same extent as if each individual publication or patent application was specifically and individually indicated to be incorporated by reference.

IV. BRIEF DESCRIPTION OF THE DRAWINGS

Figure 3:
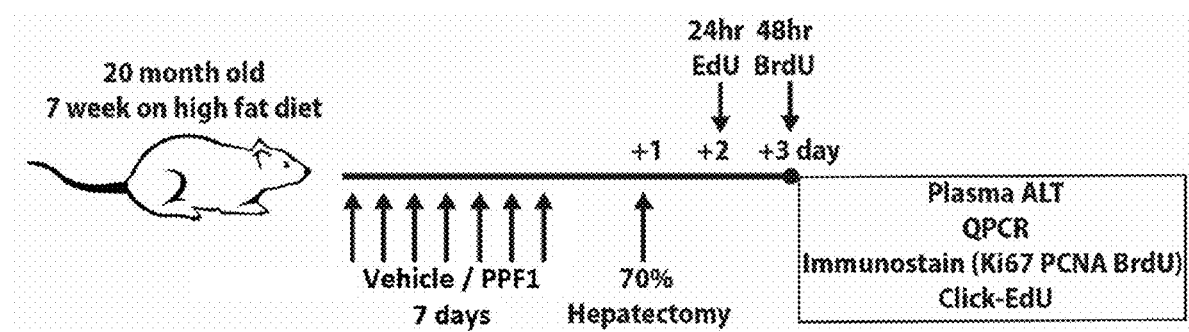

FIG. 3 shows the design of an experiment to evaluate effects of PPF1 on 20-month-old C57BL/6 mice with fatty liver. The mice were placed on a 60% high fat diet for 7 weeks prior to treatment with PPF1 or vehicle for seven consecutive days. Surgery (70% hepatectomy) was performed the day after the last dose of PPF1 or vehicle, and pre-surgery median and left lobes (resected) were removed during the hepatectomy. The right and caudate lobes (remnant) were harvested 48 hours after hepatectomy.

Figure 4:
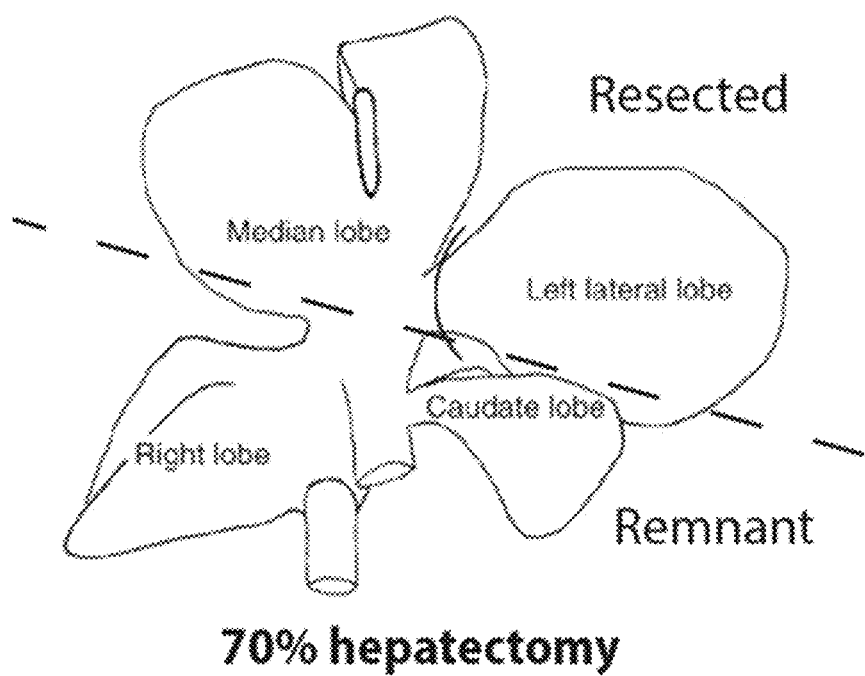

FIG. 4 identifies the resected and remnant lobes resulting from the 70% hepatectomy in mice treated as described in FIG. 3.

Figure 5:
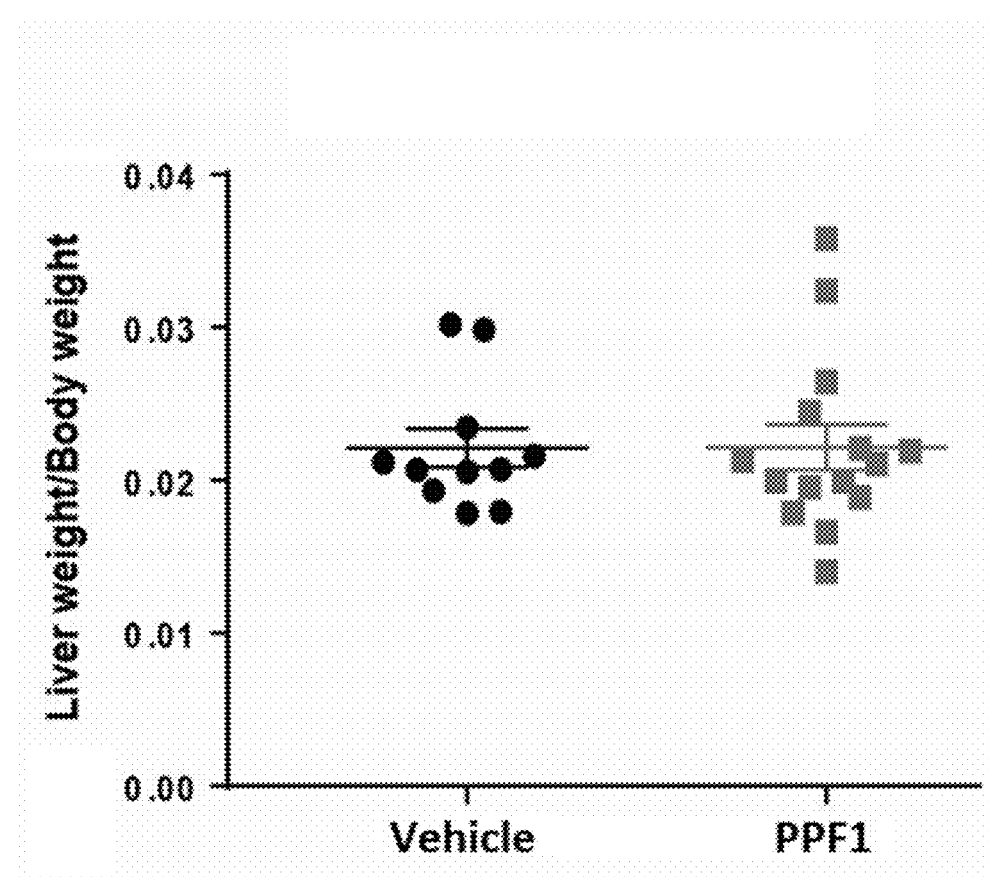

FIG. 5 shows results from the determination of the weight of the resected portion of liver to body weight ratio in vehicle and PPF1-treated hepatectomized mice treated as described in FIG. 3.

Figure 6:
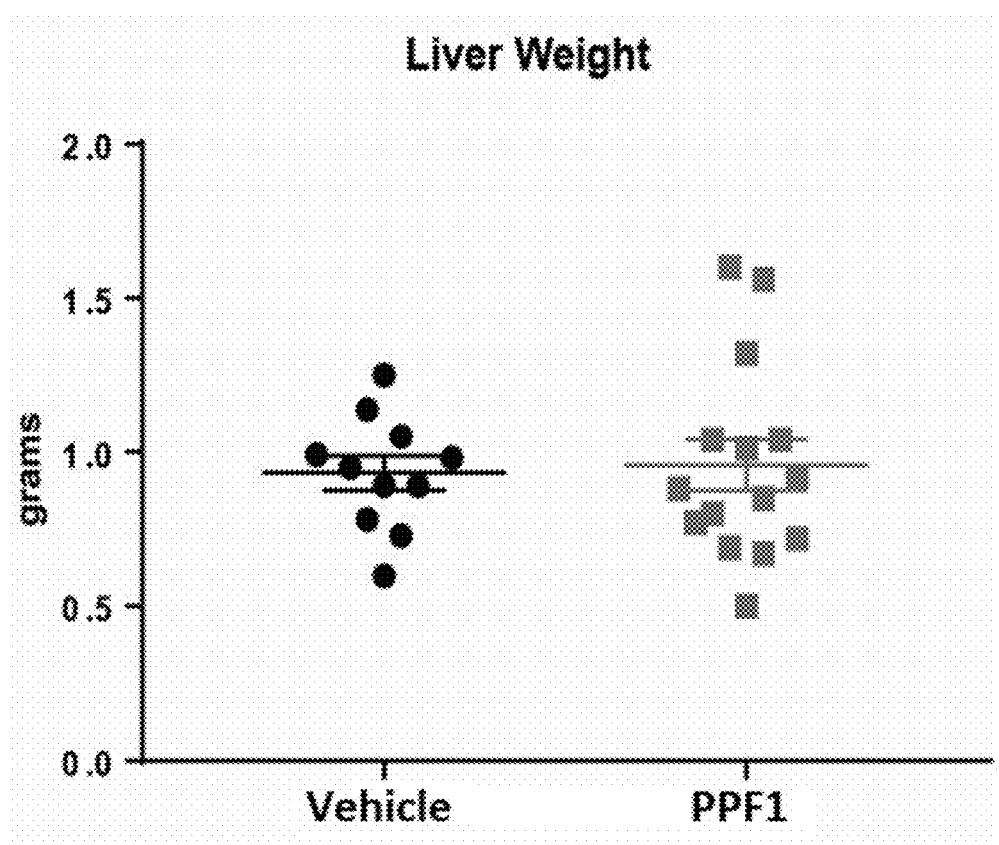

FIG. 6 shows weights of the resected portion of liver in vehicle and PPF1-treated mice treated as described in FIG. 3.

Figure 7:
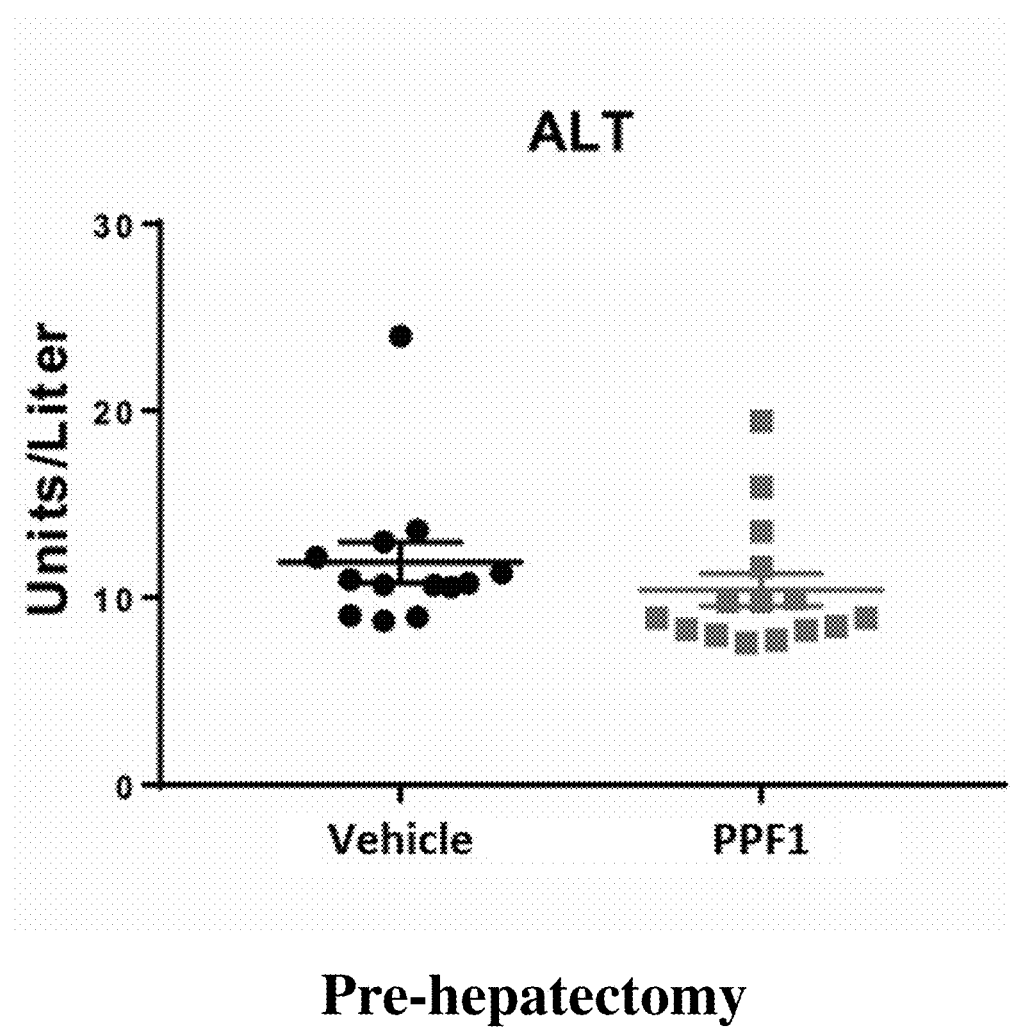
Figure 8:
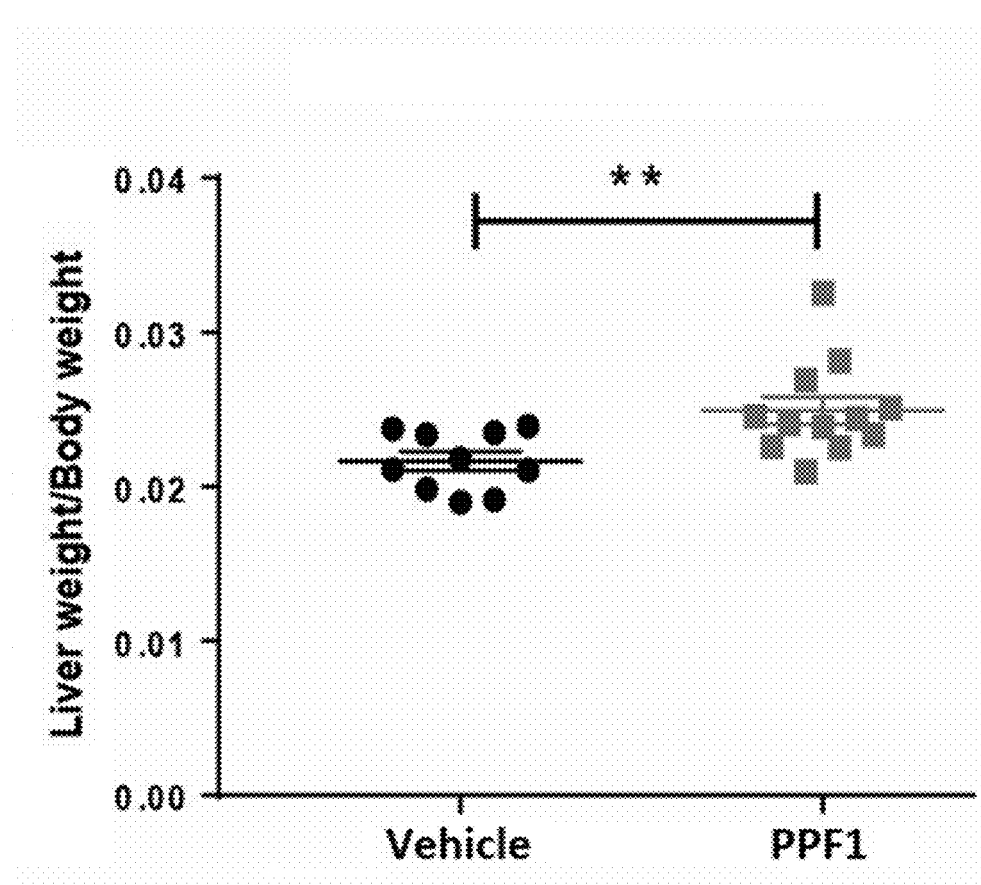

FIG. 7 is a graph showing serum ALT levels is normal and unaffected in PPF1-treated mice on HFD before hepatectomy FIG. 8 shows results from the determination of liver weight to body weight ratio in vehicle and PPF1-treated mice with remnant livers 48 hours after hepatectomy as described in FIG. 3.

Figure 9:
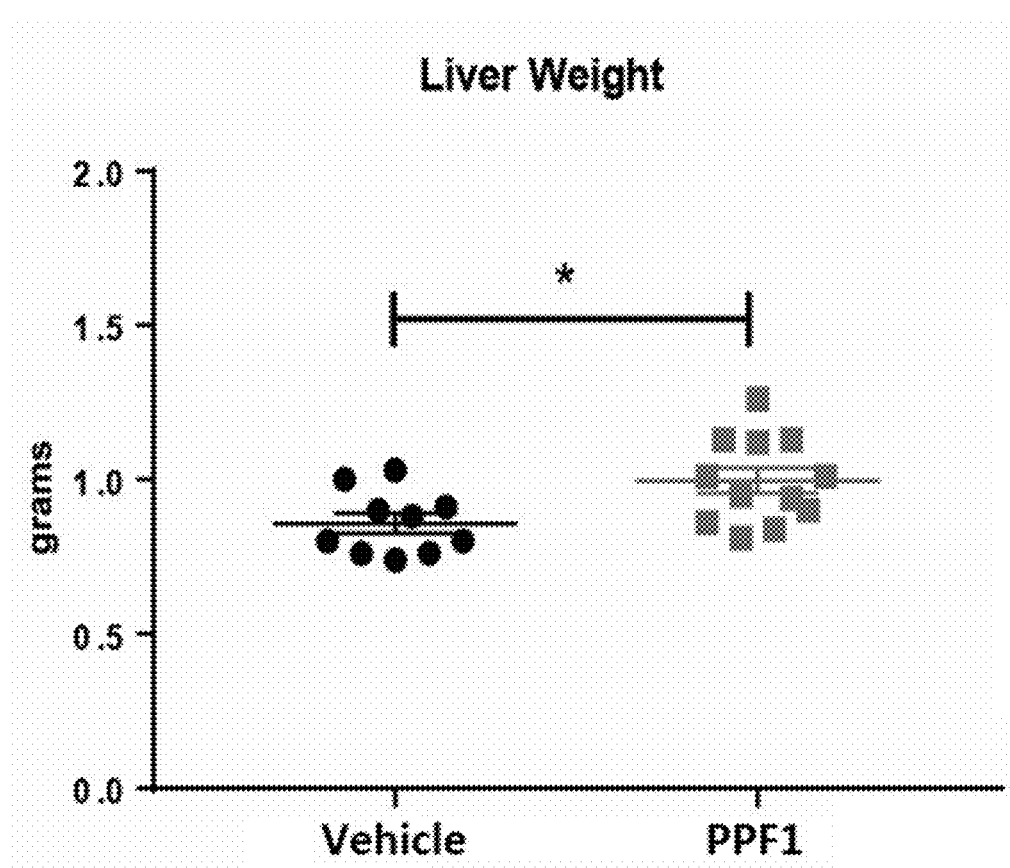

FIG. 9 shows liver weights in vehicle and PPF1-treated mice with remnant livers 48 hours after hepatectomy as described in FIG. 3.

Figure 10:
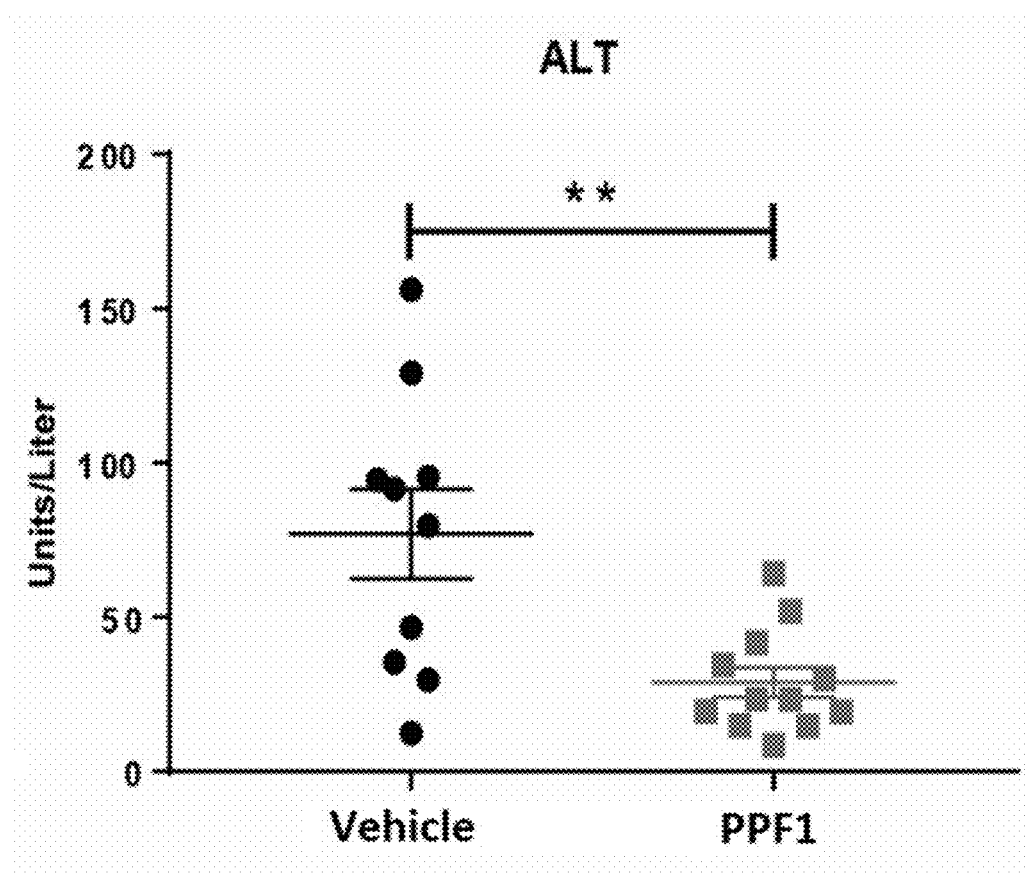

FIG. 10 shows results of serum ALT levels in vehicle and PPF1-treated mice 48 hours after hepatectomy as described in FIG. 3.

Figure 11:
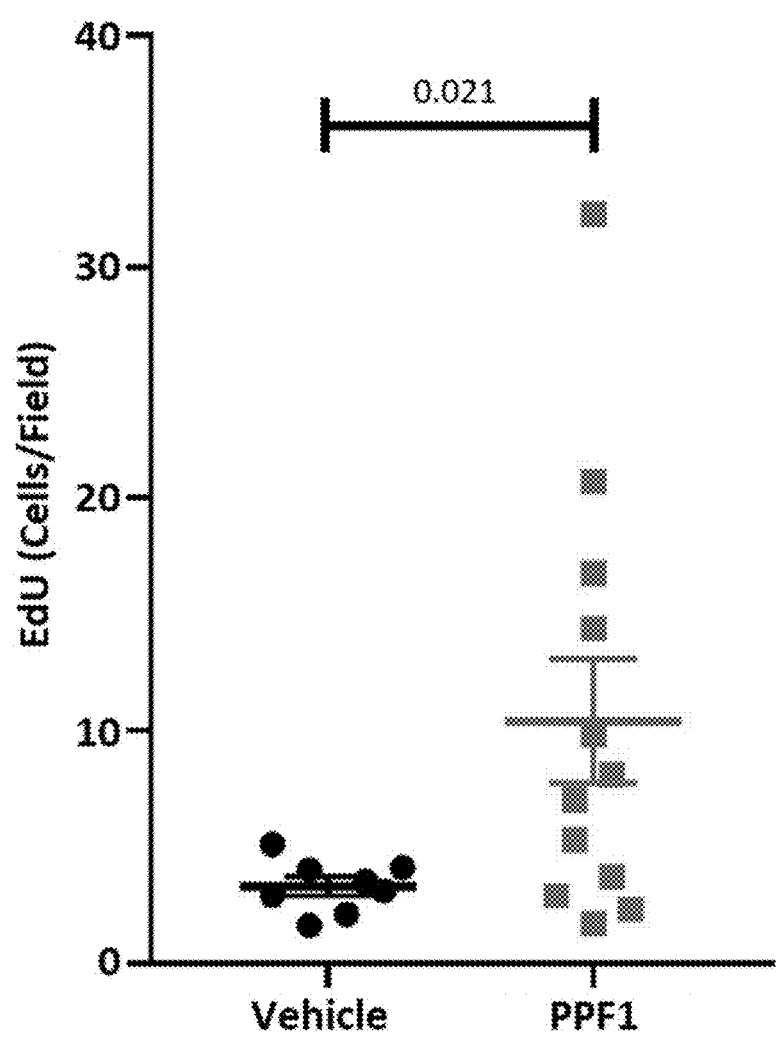

FIG. 11 reports cell proliferation rate after hepatectomy. EdU was delivered at 24-hours post-hepatectomy and the proliferation rates were traced by Click-it labeling of EdU positive cells. PPF1 significantly increased the EdU-positive number of cells per field compared to vehicle-treated animals.

Figure 12:
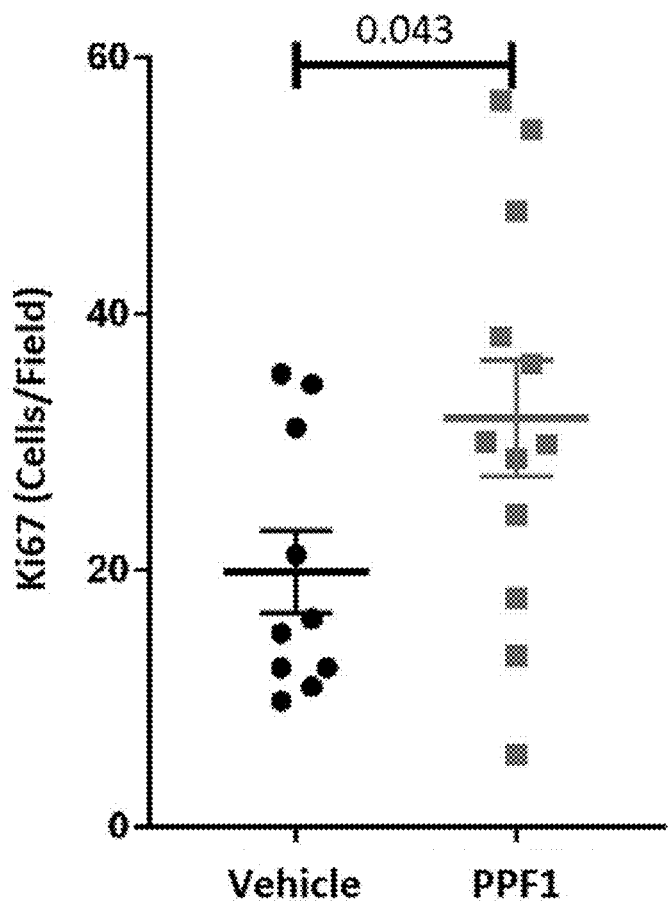

FIG. 12 reports cell proliferation at 48 hours post-hepatectomy as measured by the number of Ki67-positive cells per field. PPF1 significantly increased Ki67-positive number of cells per field compared to vehicle-treated animals.

Figure 13:
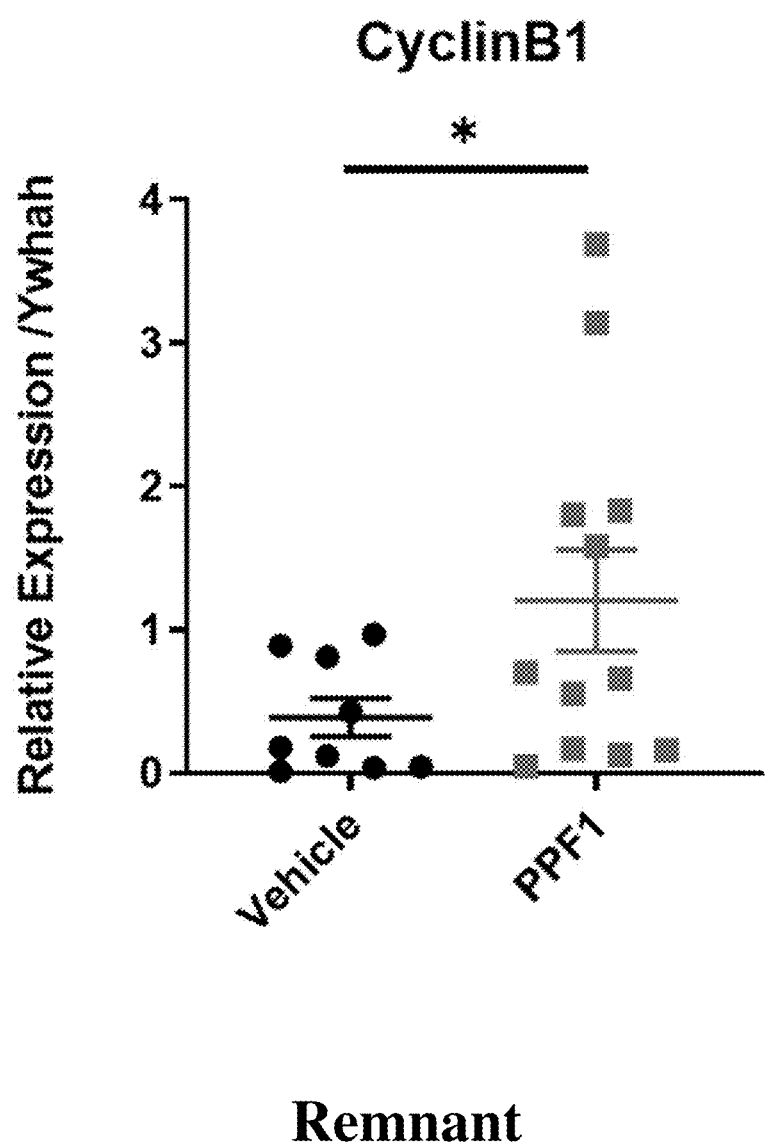

FIG. 13 reports cellular proliferation rates in remnant livers by qPCR gene expression. Relative expression of cell cycle marker Cycle B1 is shown. In remnant liver sections, Cyclin B1 expression was significantly up-regulated in PPF1-treated mice versus vehicle-treated mice.

Figure 14A:
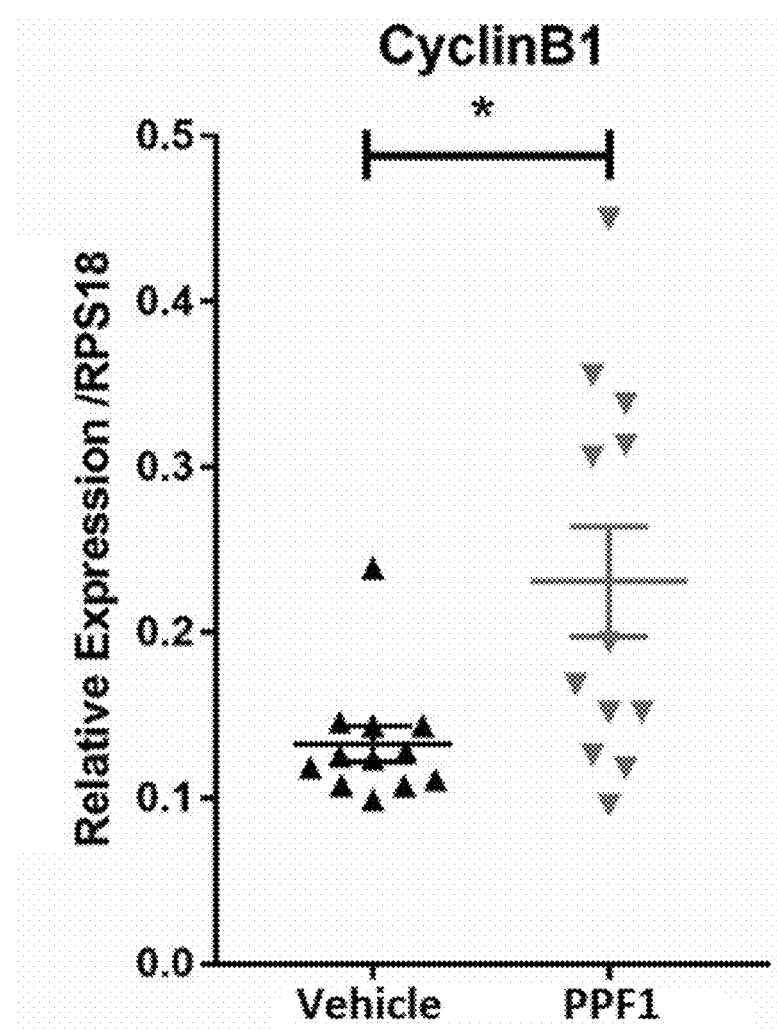
Figure 14B:
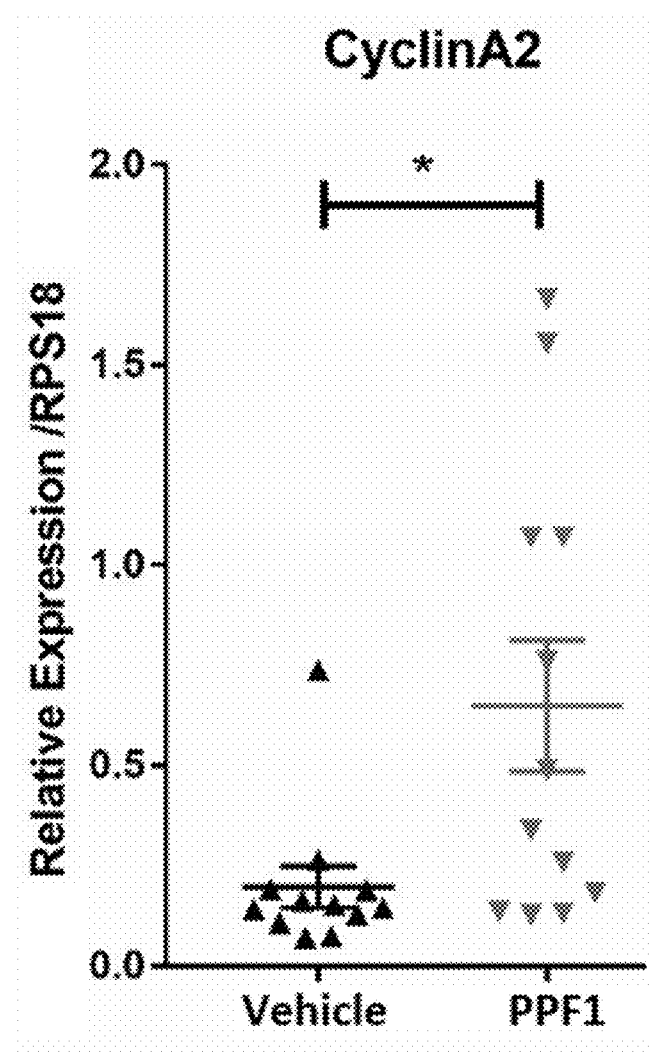
Figure 14C:
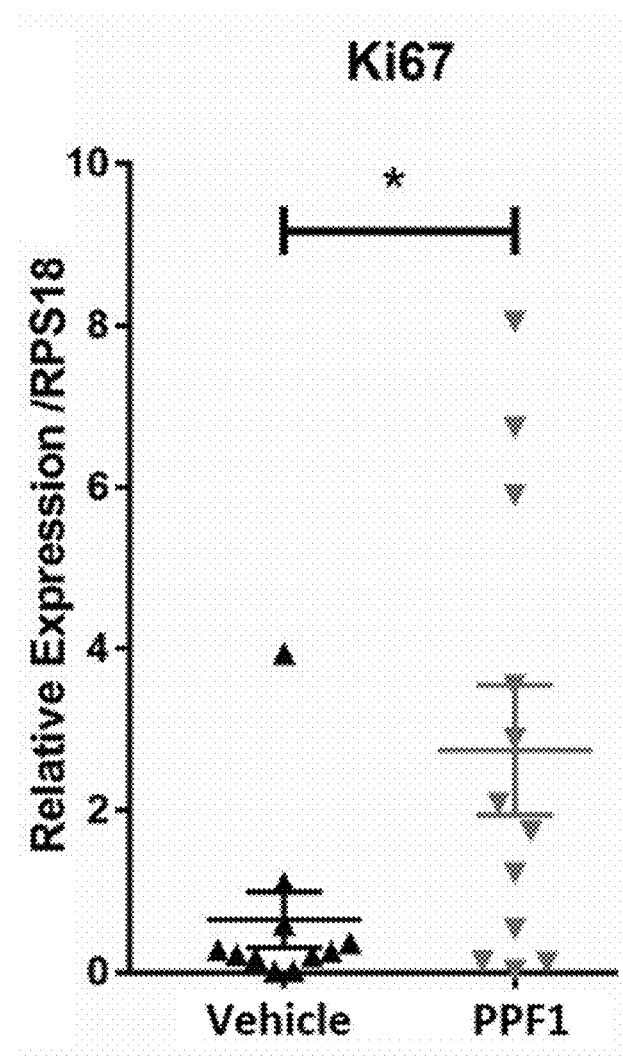
Figure 14D:
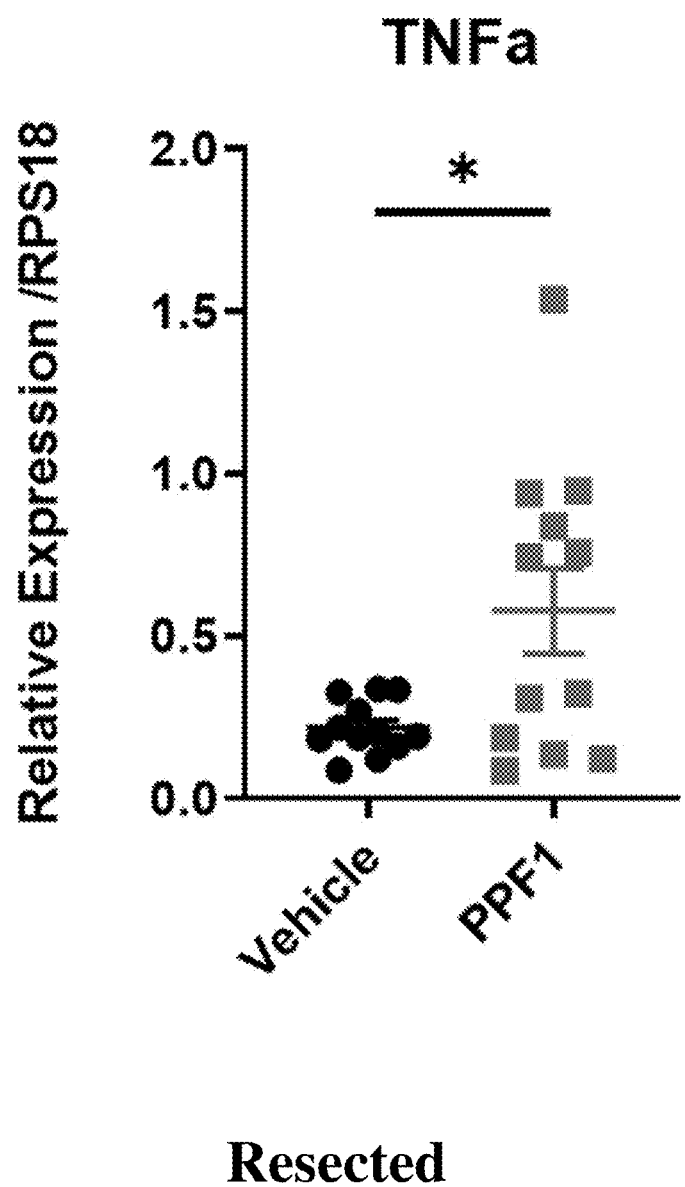

FIG. 14A through FIG. 14D report qPCR expression of several markers in resected livers by. Relative expression of cell cycle markers Cycle B1 (FIG. 14A), Cyclin A2 (FIG. 14B), and Ki67 (FIG. 14C) are shown. In resected liver sections, which were removed during hepatectomy as pre-surgery controls, PPF1 surprisingly had significantly increased cell proliferation in comparison to vehicle controls with all three cell cycle markers. FIG. 14D reports the relative expression levels of TNFα in resected liver sections. TNFα is known to contribute to the restoration of functional liver mass through driving hepatocyte proliferation during liver regeneration.

Figure 15:
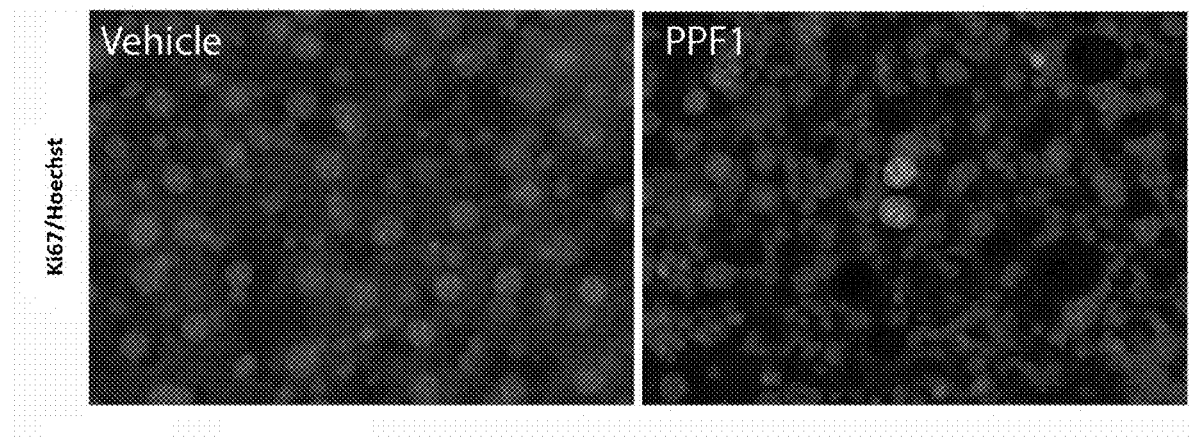

FIG. 15 shows representative images of Ki67 immunostaining in resected livers as reported in FIG. 14C, which confirms that PPF1-treated resected livers had significantly higher numbers of Ki67-positive cells in comparison to vehicle controls.

Figure 16:
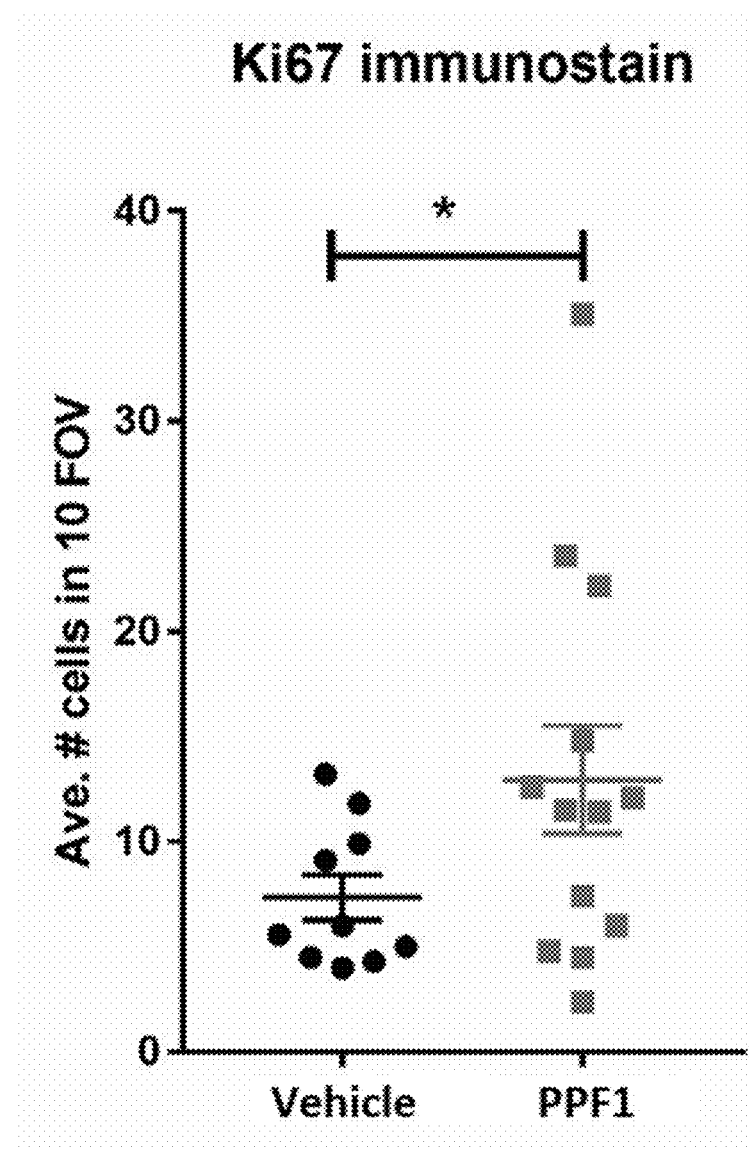

FIG. 16 reports quantification of immunostaining from FIG. 15, showing increased numbers of Ki67-positive cells in PPF1-treated resected livers.

FIG. 17 is a chart showing the total number of animals that underwent hepatectomy as well as the survival rates for each treatment.

Figure 18:
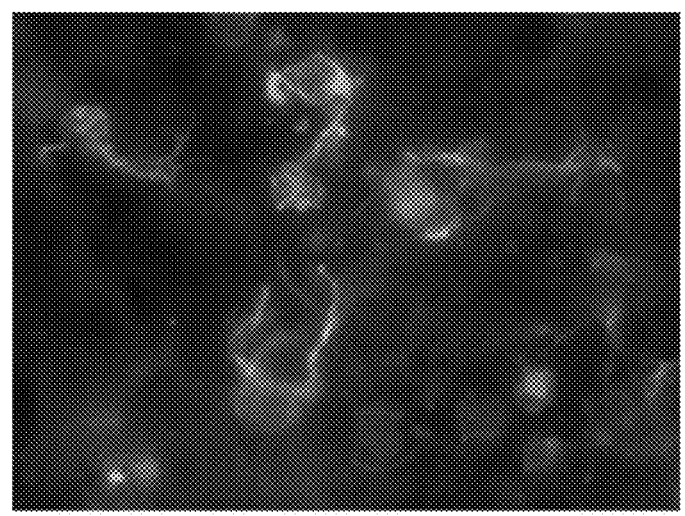
Figure 18:
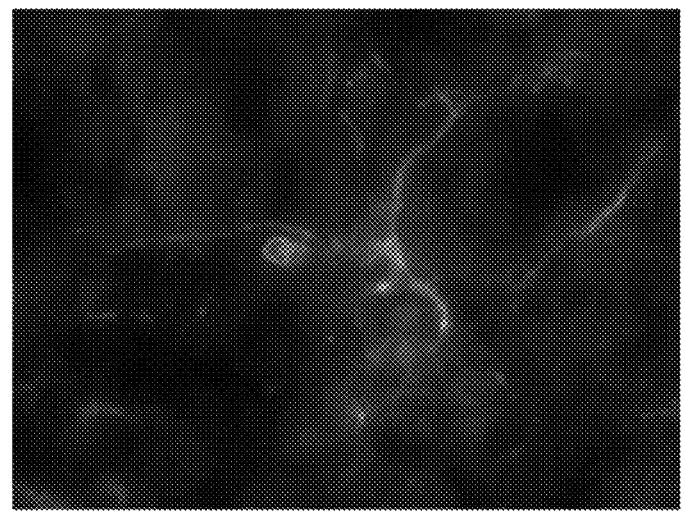

FIG. 18 displays two representative confocal microscopic fields from remnant liver incorporated with EdU 24 hours after hepatectomy (See FIG. 3). Histologic sections were stained with GFAP antibody (stellate cell marker) and levels of colocalization with EdU with GFAP observed. It was determined from the lack of colocalization between EdU and GFAP that cell proliferation associated with PPF1 administration did not occur in stellate cells.

Figure 19:
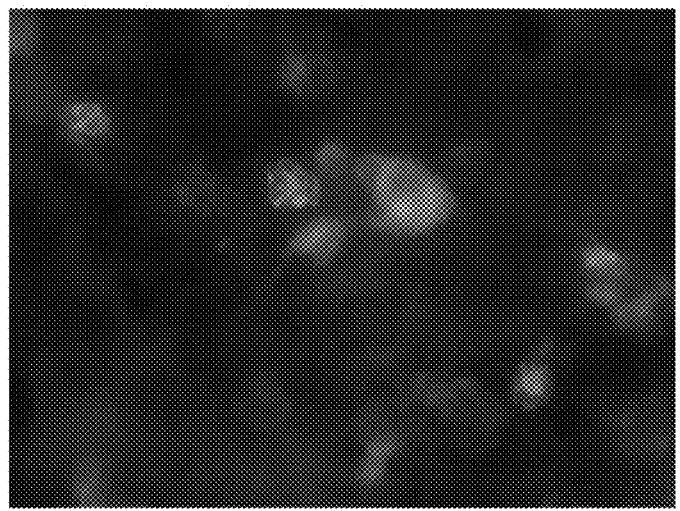
Figure 19:
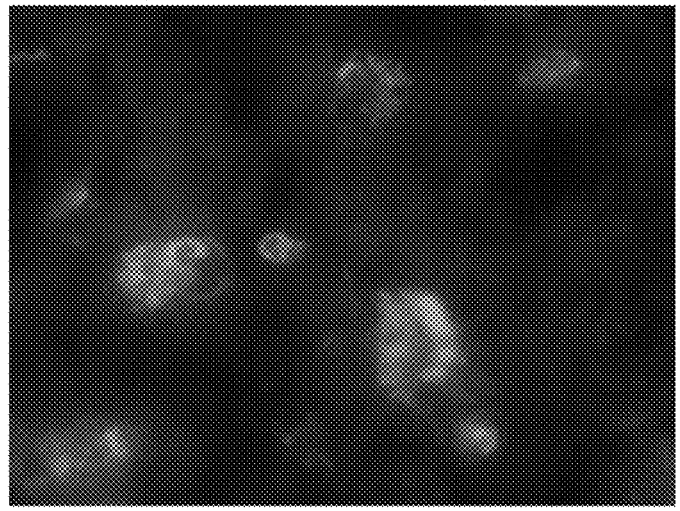

FIG. 19 displays two representative confocal microscopic fields from remnant liver incorporated with EdU 24 hours after hepatectomy (See FIG. 3). The histologic sections were stained with CD68 antibody (Kupffer cell marker) and levels of colocalization with EdU with CD68 observed. It was determined from the lack of colocalization between EdU and CD68 that cell proliferation associated with PPF1 administration did not occur in Kupffer cells.

Figure 20:
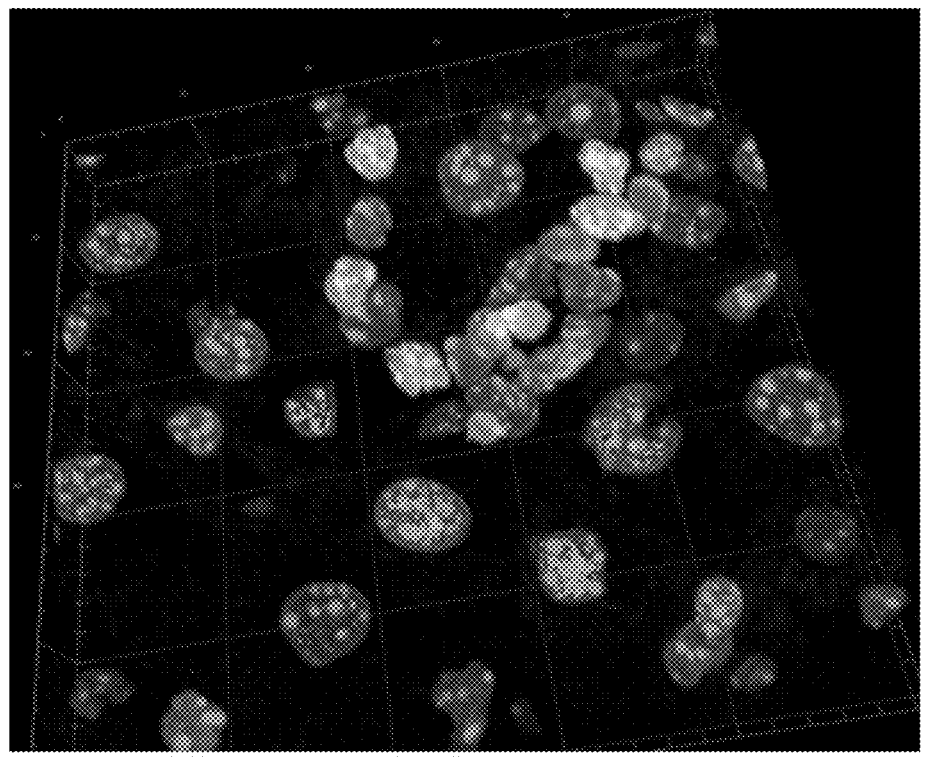

FIG. 20 displays a representative confocal microscopic field from remnant liver incorporated with EdU 24 hours after hepatectomy (See FIG. 3). The histologic section was stained with HNF4a antibody (hepatocyte cell marker) and levels of colocalization with EdU with HNF4a observed. It was determined from the lack of colocalization between EdU and HNF4a that cell proliferation associated with PPF1 administration did not occur in hepatocytes.

Figure 21:
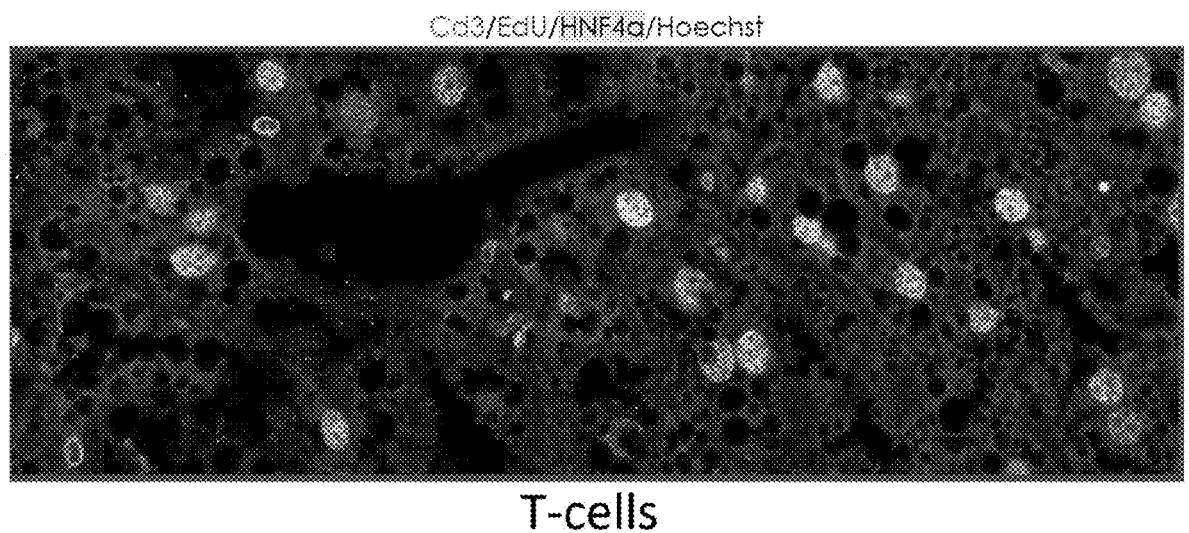

FIG. 21 displays a representative confocal microscopic field from remnant liver incorporated with EdU 24 hours after hepatectomy (See FIG. 3). The histologic section was stained with CD3 antibody (T-cell marker) and levels of colocalization with EdU with CD3 observed. It was determined from the lack of colocalization between EdU and CD3 that cell proliferation associated with PPF1 administration did not occur in T-cells.

Figure 22:
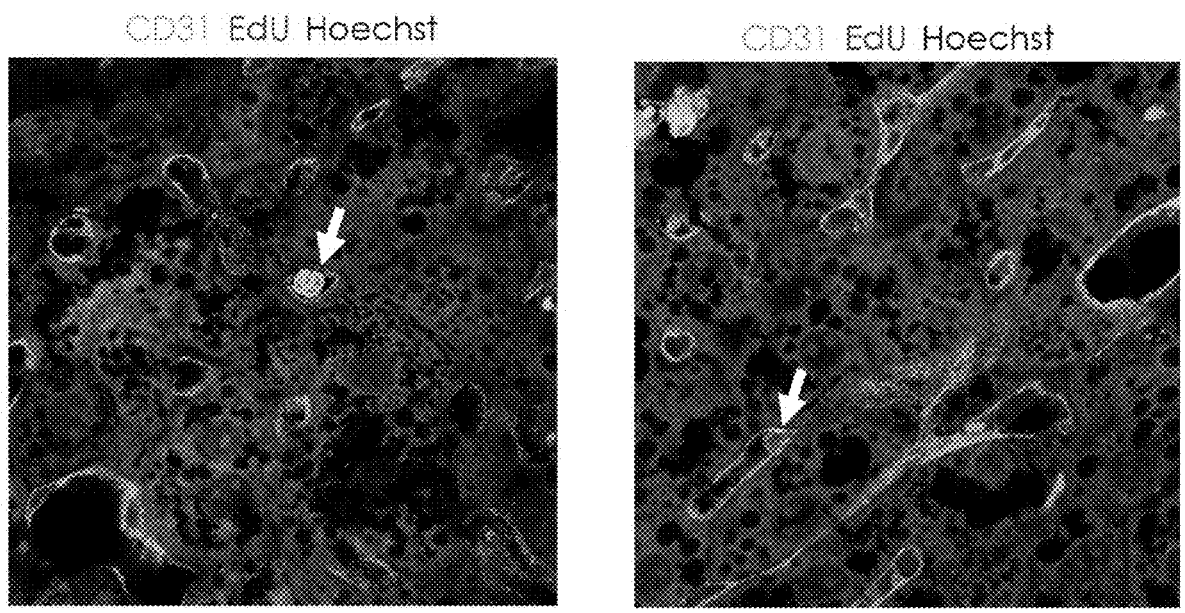

FIG. 22 displays two representative confocal microscopic fields from remnant liver incorporated with EdU 24 hours after hepatectomy (See FIG. 3). The histologic sections were stained with CD31 antibody (sinusoidal endothelial cell marker) and levels of colocalization of EdU with CD31 observed. It was determined from a positive colocalization between EdU and CD31 that cell proliferation caused by PPF1 administration is associated with liver sinusoidal endothelial cells (LSECs). Arrows indicate LSECs that include EdU positive cells.

Figure 23:
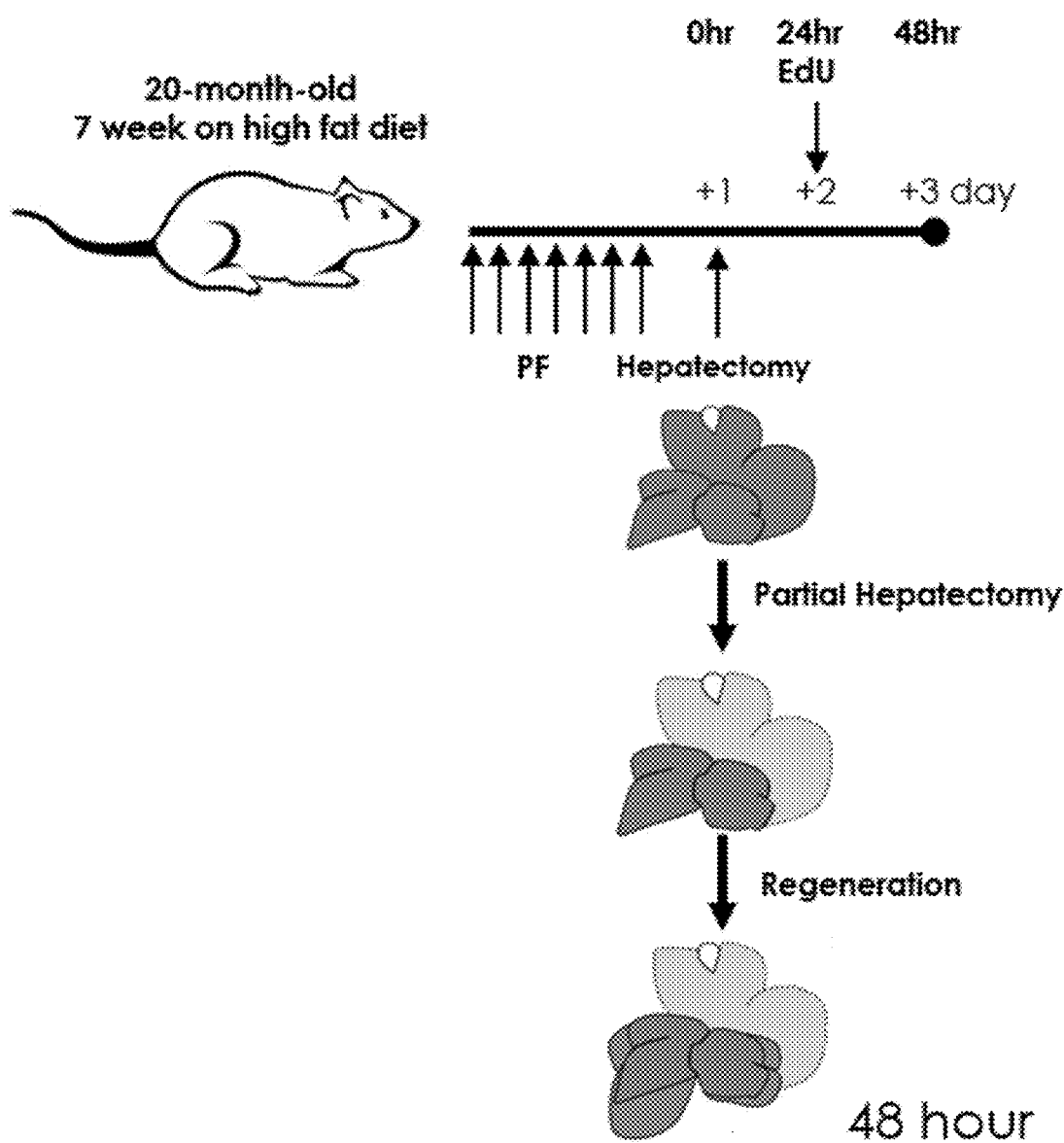

FIG. 23 shows the design of an experiment to evaluate effects of PPF1 (a plasma fraction "PF") and recombinant human albumin (rhAlbumin) on 20-month-old C57BL/6 mice. The mice were placed on a 60% high fat diet for 8 weeks prior to treatment with PPF1, rhAlbumin, or vehicle for seven consecutive days. Surgery (70% hepatectomy) was performed the day after the last dose of PPF1, rhAlbumin, or vehicle, and pre-surgery median and left lobes (resected) were removed during the hepatectomy. The right and caudate lobes (remnant) were harvested 48 hours after hepatectomy.

Figure 24:
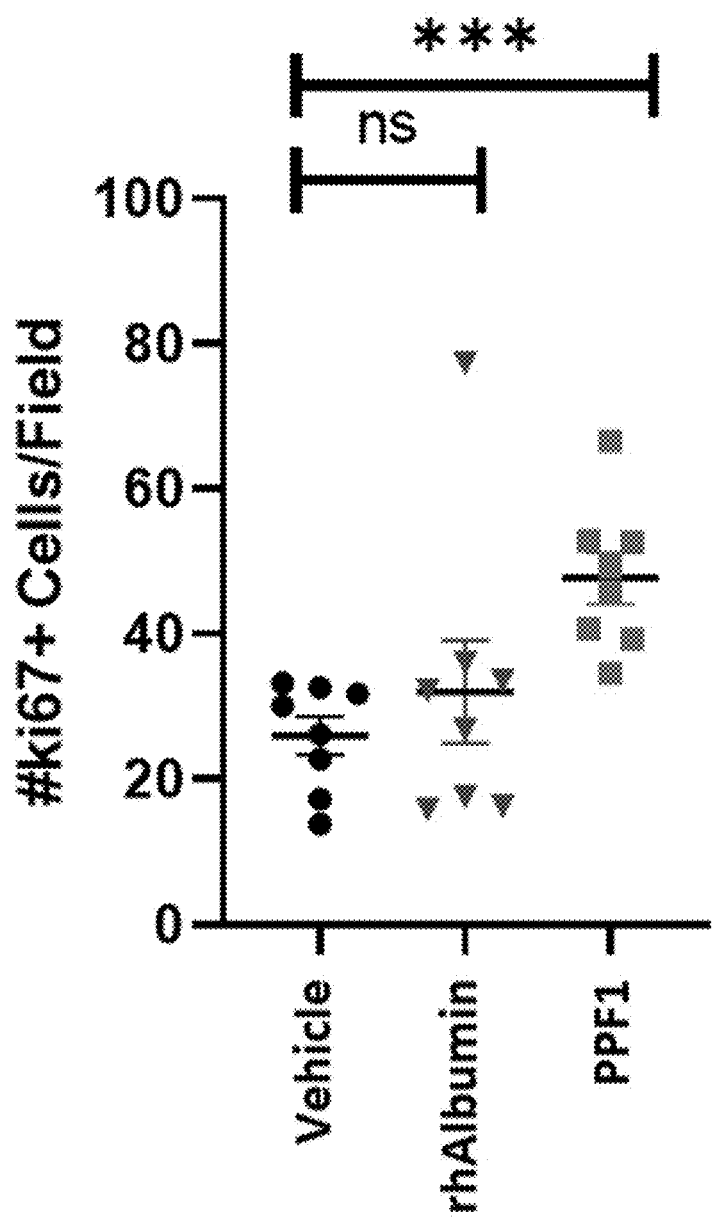

FIG. 24 reports cell proliferation at 48 hours post-hepatectomy in resected livers as measured by the number of Ki67-positive cells per field. PPF1 significantly increased Ki67-positive number of cells per field compared to vehicle-treated animals. In contrast, rhAlbumin-treated animals exhibited no significant difference from vehicle-treated animals.

Figure 25:
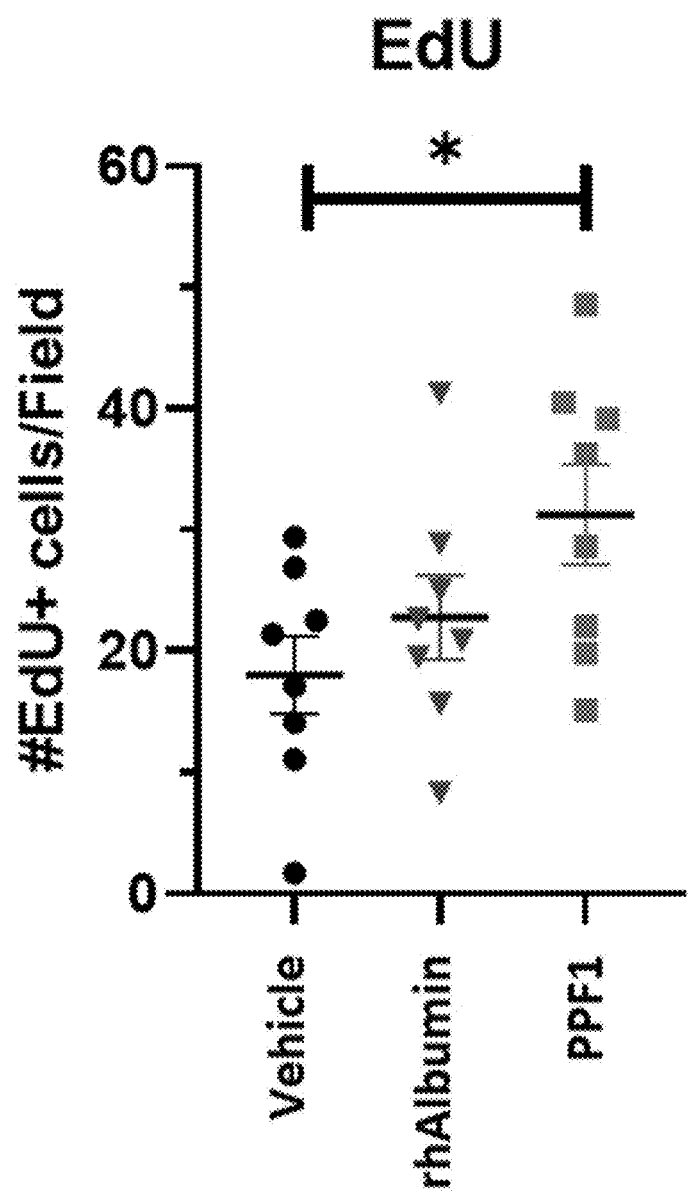

FIG. 25 reports cell proliferation rate after hepatectomy in remnant livers. EdU was delivered at 24-hours post-hepatectomy and the proliferation rates were traced by click-chemistry. PPF1 significantly increased the EdU-positive number of cells per field compared to vehicle-treated animals. In contrast, rhAlbumin-treated animals exhibited a less significant trend in proliferation compared vehicle-treated animals.

Figure 26:
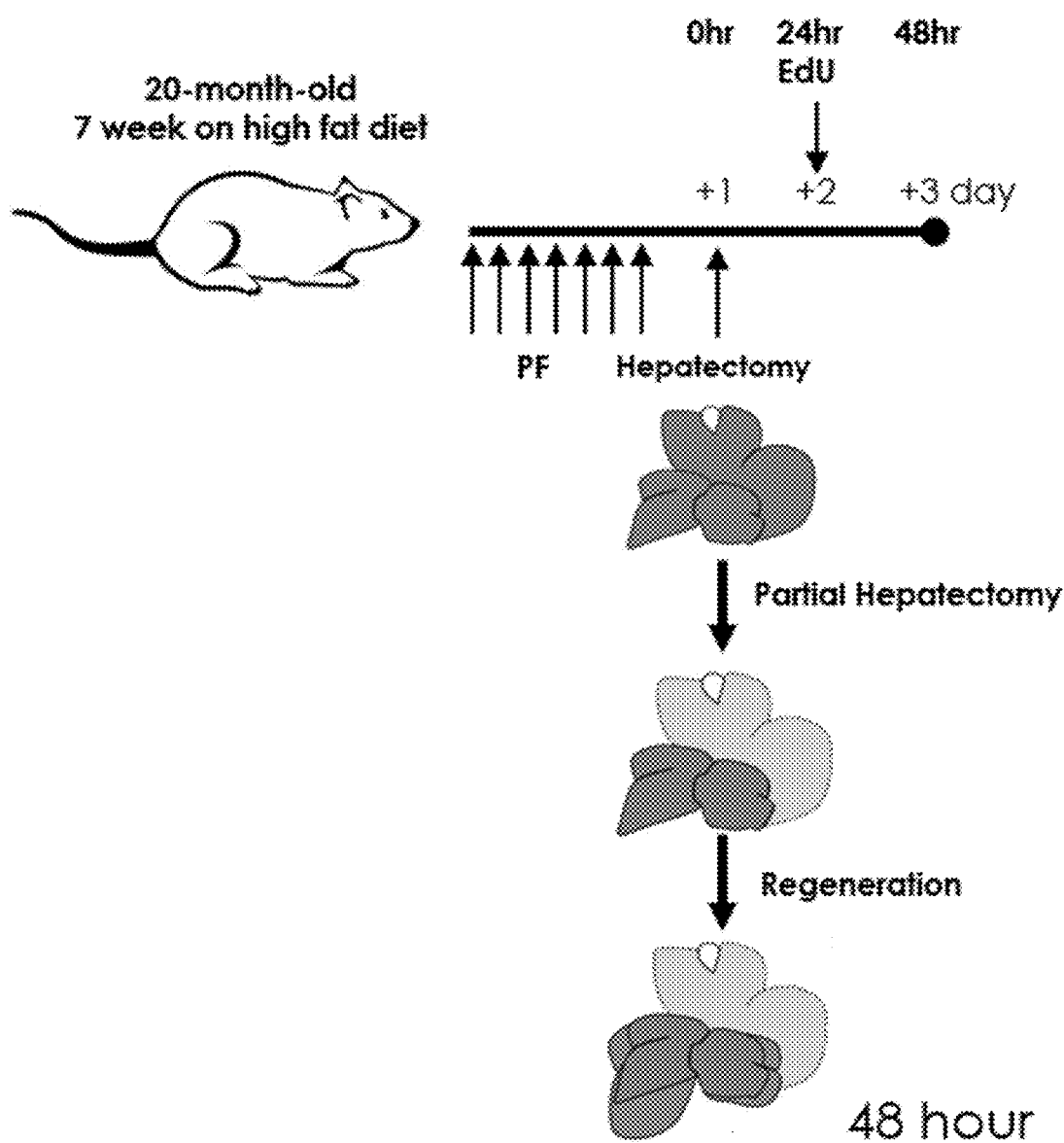

FIG. 26 shows the design of an experiment to evaluate the effects of PPF1 and HAS1 on 20-month-old C57BL/6 mice. The mice were placed on a 60% high fat diet for 8 weeks prior to treatment with the different plasma fractions (PF) PPF1 and HAS1 or vehicle for seven consecutive days. Surgery (70% hepatectomy) was performed the day after the last dose of PPF1, HAS1, or vehicle treatment, and pre-surgery median and left loves (resected) were removed during the hepatectomy. The right and caudate lobes (remnant) were harvested 48 hours after hepatectomy.

Figure 27:
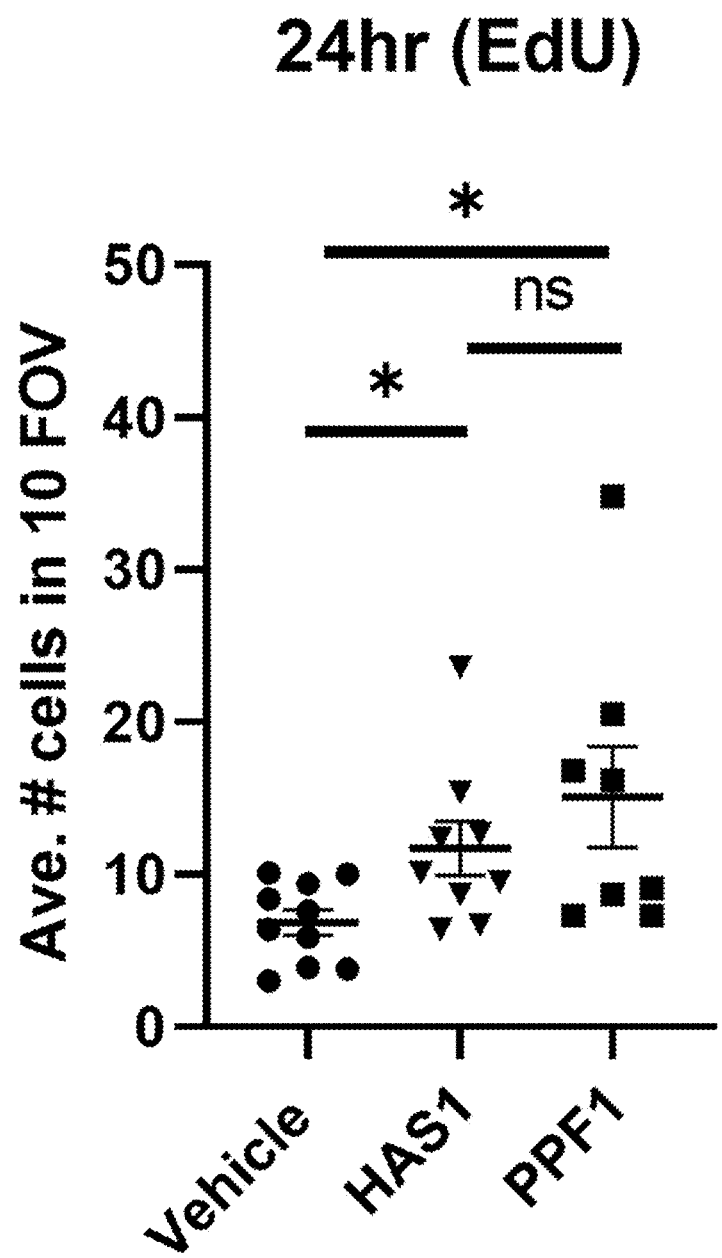

FIG. 27 reports cell proliferation rates 24 hours after hepatectomy. EdU was delivered at 24-hours post-hepatectomy. Both PPF1 and HAS1 significantly increased EdU-positive number of cells in comparison to vehicle in remnant livers.

Figure 28:
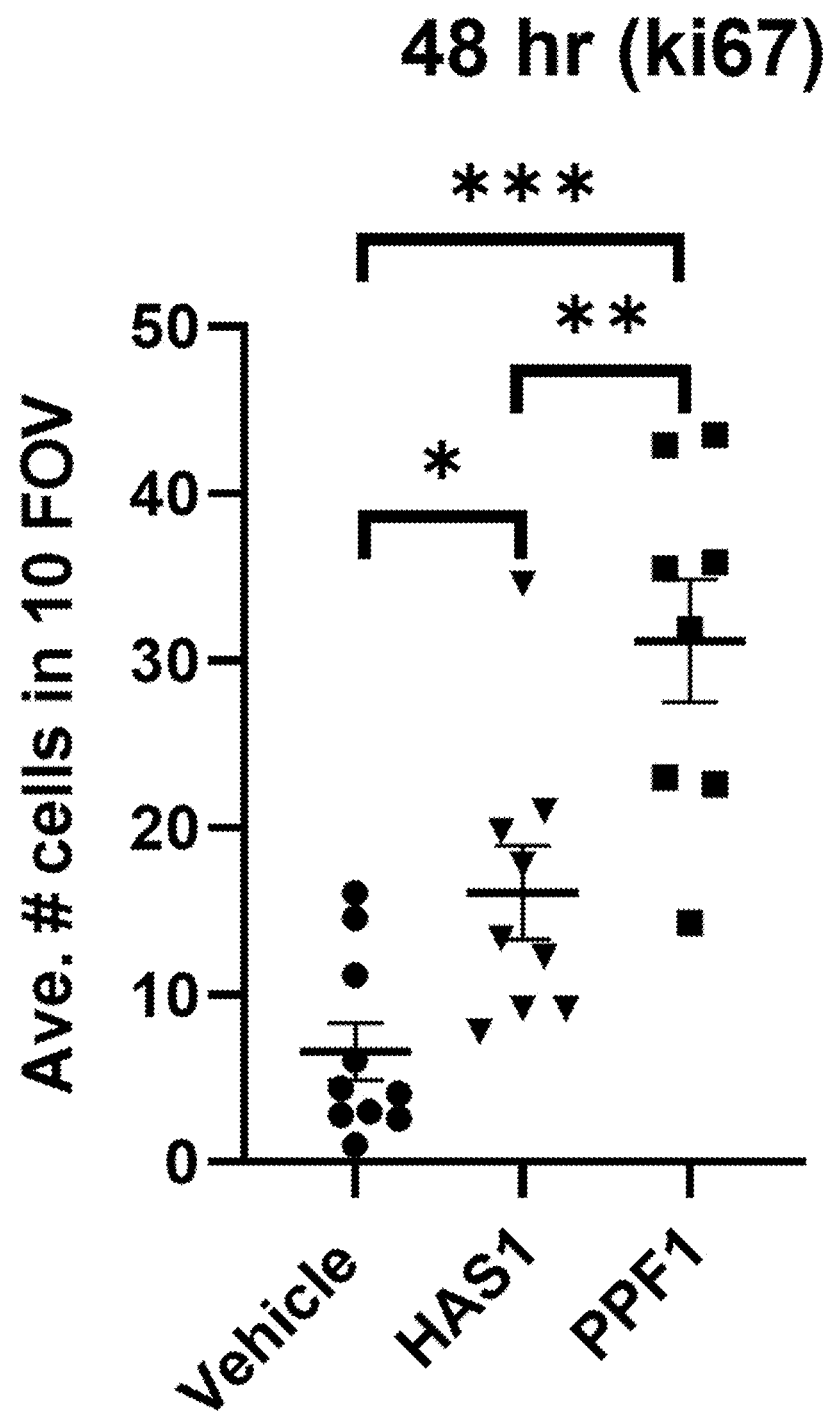

FIG. 28 shows cell proliferation rates 48 hours after hepatectomy. Ki67 immunostaining was performed on remnant liver taken out 48 hours after hepatectomy. While both PPF1 and HAS significantly increased cellular proliferation in comparison to control animals, PPF1 also induced significantly more proliferation in comparison to HAS1-treated animals.

Figure 29:
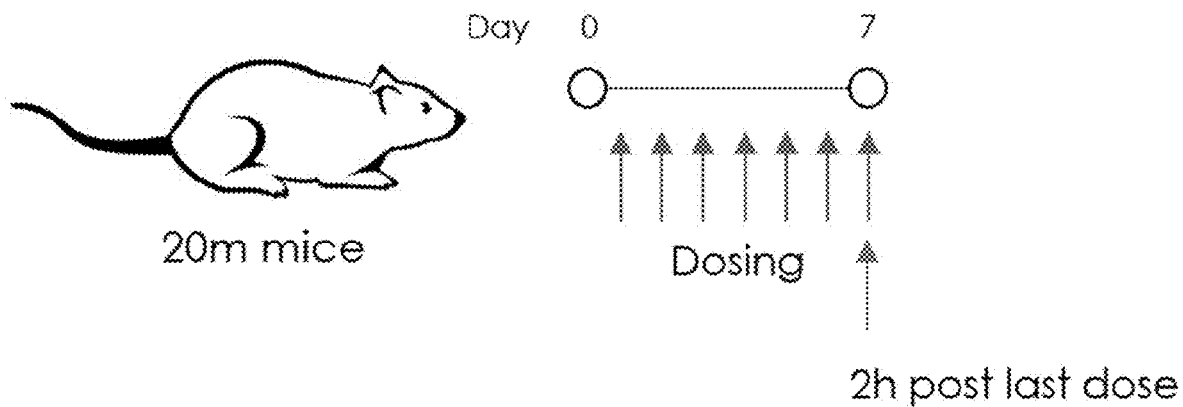

FIG. 29 shows the design of an experiment to evaluate the effects of PPF1 2 hours after last dose on 20-month-old C57BL/6 mice.

Figure 30:
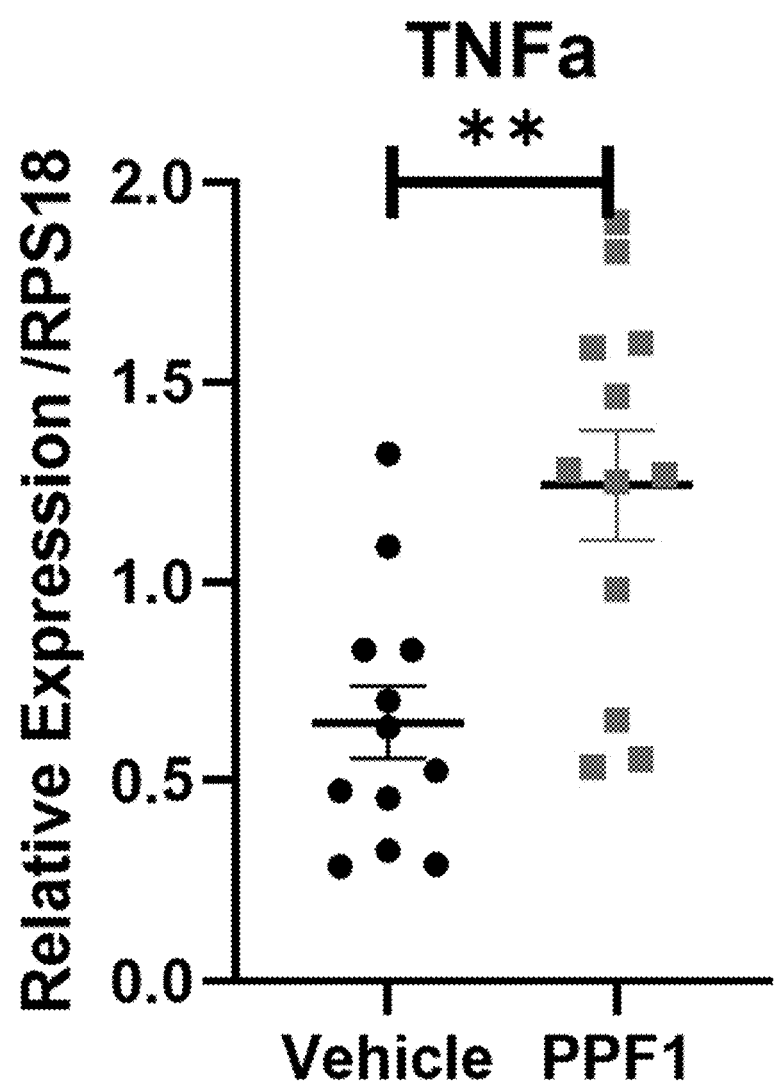

FIG. 30 shows results of TNFα gene expression analysis on mice treated as described in FIG. 29 above. In comparison to vehicle treated animals, PPF1 treated animals had a significant increase in TNFα gene expression by QPCR.

Figure 31:
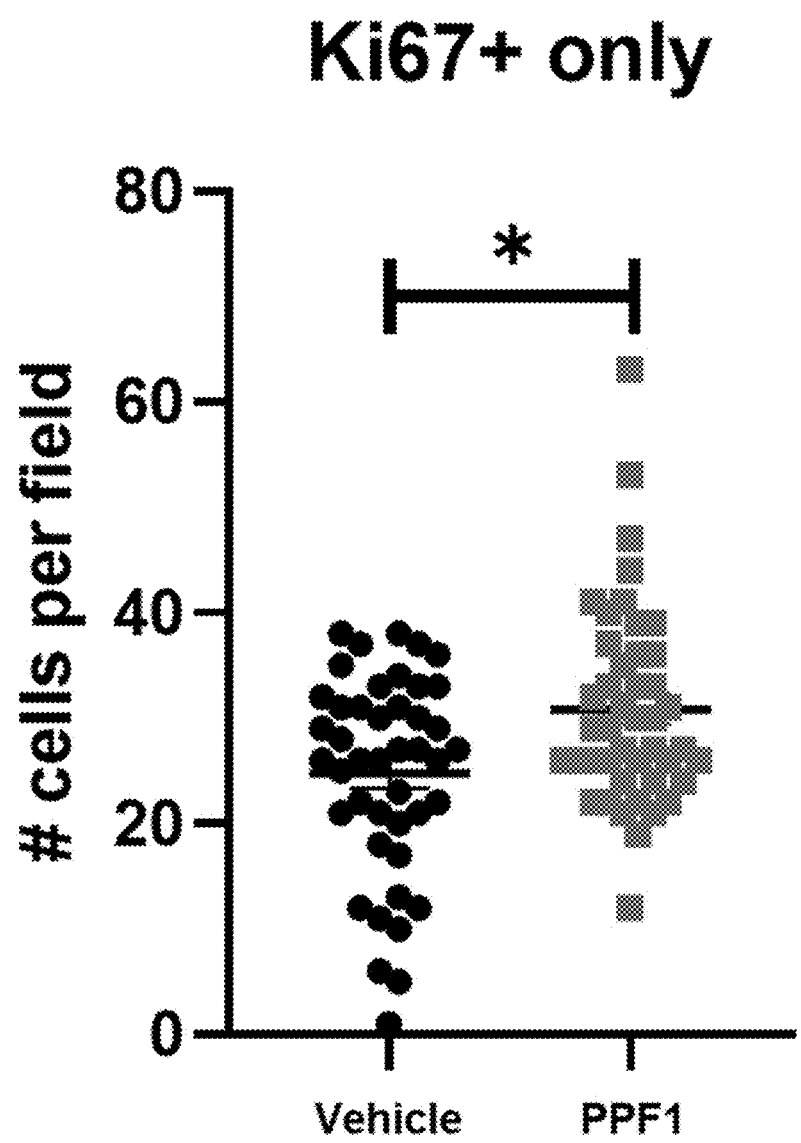

FIG. 31 shows results of Ki67 immunostaining analysis on mice treated as described in FIG. 29 above. In comparison to vehicle treated animals, PPF1 treated animals at 2-hours after the last dose significantly increased Ki67-positive cells indicating an increase of liver cellular proliferation by PPF1.

V. DETAILED DESCRIPTION OF THE INVENTION

A. Introduction

The present invention relates to the treatment of disorders or diseases of the liver. Plasma fractions including products of blood plasma fractionation are shown to have marked activity in inducing recovery of livers after hepatectomy. Additionally, plasma fractions are shown to activate cell proliferation in quiescent and intact livers (before hepatectomy). Plasma fractions present several advantages over whole plasma serum since the blood plasma fractionation process can remove problematic coagulation factors as well as obviate the need for blood cross-matching. Additionally, plasma fractions have exhibited unexpected improvement in efficacy compared to young plasma in certain analyses (see, e.g., U.S. patent application Ser. No. 15/499,694 and U.S. patent application Ser. No. 16/432,114; and which are both incorporated by reference herein in their entirety). Thus, predicting efficacy from whole plasma serum to products of plasma fractionation is not subject to reasonable predictability.

Before describing the present invention in detail, it is to be understood that this invention is not limited to a particular method or composition described, as such may, of course, vary. It is also understood that the terminology used herein is for the purpose of describing particular embodiments only, and is not intended to be limiting, since the scope of the present invention will be limited only by the appended claims.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

It is noted that the claims may be drafted to exclude any optional element. As such, this statement is intended to serve as antecedent basis for use of such exclusive terminology as "solely," "only" and the like in connection with the recitation of claim elements or use of a "negative" limitation.

As will be apparent to those of skill in the art upon reading this disclosure, each of the individual embodiments described and illustrated herein have discrete components and features which may be readily separated from or combined with the features of any of the other several embodiments without departing from the scope or the spirit of the present invention. Any recited method can be carried out in the order of events recited or in any other order which is logically possible.

B. Definitions

Unless otherwise defined, all technical and scientific terms used herein have the same meaning as commonly understood by one having ordinary skill in the art to which the invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a," "an," and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those having skill in the art, and so forth.

In describing methods of the present invention, the terms "host", "subject", "individual" and "patient" are used interchangeably and refer to any mammal in need of such treatment according to the disclosed methods. Such mammals include, e.g., humans, ovines, bovines, equines, porcines, canines, felines, non-human primate, mice, and rats. In certain embodiments, the subject is a non-human mammal. In some embodiments, the subject is a farm animal. In other embodiments, the subject is a pet. In some embodiments, the subject is mammalian. In certain instances, the subject is human. Other subjects can include domestic pets (e.g., dogs and cats), livestock (e.g., cows, pigs, goats, horses, and the like), rodents (e.g., mice, guinea pigs, and rats, e.g., as in animal models of disease), as well as non-human primates (e.g., chimpanzees, and monkeys). As such, subjects of the invention, include but are not limited to mammals, e.g., humans and other primates, such as chimpanzees and other apes and monkey species; and the like, where in certain embodiments the subject are humans. The term subject is also meant to include a person or organism of any age, weight or other physical characteristic, where the subjects may be an adult, a child, an infant or a newborn.

By a "young" or "young individual" it is meant an individual that is of chronological age of 40 years old or younger, e.g., 35 years old or younger, including 30 years old or younger, e.g., 25 years old or younger or 22 years old or younger. In some instances, the individual that serves as the source of the young plasma-comprising blood product is one that is 10 years old or younger, e.g., 5 years old or younger, including 1-year-old or younger. In some instances, the subject is a newborn and the source of the plasma product is the umbilical cord, where the plasma product is harvested from the umbilical cord of the newborn. As such, "young" and "young individual" may refer to a subject that is between the ages of 0 and 40, e.g., 0, 1, 5, 10, 15, 20, 25, 30, 35, or 40 years old. In other instances, "young" and "young individual" may refer to a biological (as opposed to chronological) age such as an individual who has not exhibited the levels of inflammatory cytokines in the plasma exhibited in comparatively older individuals. Conversely, these "young" and "young individual" may refer to a biological (as opposed to chronological) age such as an individual who exhibits greater levels of anti-inflammatory cytokines in the plasma compared to levels in comparatively older individuals. By way of example, and not limitation, the inflammatory cytokine is Eotaxin, and the fold difference between a young subject or young individual and older individuals is at least 1.5-fold. Similarly, the fold difference between older and younger individuals in other inflammatory cytokines may be used to refer to a biological age. (See U.S. patent application Ser. No. 13/575,437 which is herein incorporated by reference). Usually, the individual is healthy, e.g., the individual has no hematological malignancy or autoimmune disease at the time of harvest.

As used herein, "treatment" refers to any of (i) the prevention of the disease or disorder, or (ii) the reduction or elimination of symptoms of the disease or disorder. Treatment may be effected prophylactically (prior to the onset of a liver disorder or liver failure and includes: (a) preventing the condition from occurring in a subject; (b) inhibiting the condition, i.e., arresting its occurrence; or (c) relieving the condition, i.e., causing regression of the condition. Treatment may result in a variety of different physical manifestations, e.g., modulation in gene expression, rejuvenation of tissue or organs, decreasing inflammation, etc. The therapeutic agent may be administered before, during or after the onset of the condition. The subject therapy may be administered during the symptomatic stage of the condition, and in some cases after the symptomatic stage of the condition. Treatment may also be effected by administration of an intervention such as a blood plasma, blood plasma fraction, or blood product comprising plasma components prior to liver resection or transplantation, during liver resection/transplantation, and/or after liver resection/transplantation.

"Improving," "improvement," or "improved" as it relates to liver function, regeneration, or recovery is meant any appreciable increase in liver function as measured using standard methodology known in the field. By way of example and not limitation, this may include measuring blood levels of certain proteins such as alanine transaminase (ALT), aspartate transaminase (AST), alkaline phosphatase (ALP), albumin and total protein, bilirubin, gamma-glutamyltransferase (GGT), L-lactate dehydrogenase (LD), prothrombin time (PT). Examples of normal levels of said proteins can be: ALT (7 to 55 U/L); AST (8 to 48 U/L); ALP (40 to 129 U/L); albumin (3.5 to 5.0 g/dL); total protein (6.3 to 7.9 g/dL); bilirubin (0.1 to 1.2 mg/dL); GGT (8 to 61 U/L); LD (122 to 222 U/L); and PT (9.4 to 12.5 seconds).

Blood Products Comprising Plasma Components. In practicing the subject methods, a blood product comprising plasma components is administered to an individual in need thereof, e.g., an individual suffering from one or more of the following conditions: a liver disorder or liver failure. As such, methods according to embodiments of the invention include administering a blood product comprising plasma components from an individual (the "donor individual", or "donor") to an individual suffering from one or more of the following conditions: a liver disorder or liver failure (the "recipient individual" or "recipient"). By a "blood product comprising plasma components," it is meant any product derived from blood that comprises plasma (e.g. whole blood, blood plasma, or fractions thereof). The term "plasma" is used in its conventional sense to refer to the straw-colored/pale-yellow liquid component of blood composed of about 92% water, 7% proteins such as albumin, gamma globulin, anti-hemophilic factor, and other clotting factors, and 1% mineral salts, sugars, fats, hormones and vitamins. Non-limiting examples of plasma-comprising blood products suitable for use in the subject methods include whole blood treated with anti-coagulant (e.g., EDTA, citrate, oxalate, heparin, etc.), blood products produced by filtering whole blood to remove white blood cells ("leukoreduction"), blood products consisting of plasmapheretically-derived or apheretically-derived plasma, fresh-frozen plasma, blood products consisting essentially of purified plasma, and blood products consisting essentially of plasma fractions. In some instances, plasma product that is employed is a non-whole blood plasma product, by which is meant that the product is not whole blood, such that it lacks one or more components found in whole blood, such as erythrocytes, leukocytes, etc., at least to the extent that these components are present in whole blood. In some instances, the plasma product is substantially, if not completely, acellular, where in such instances the cellular content may be 5% by volume or less, such as 1% or less, including 0.5% or less, where in some instances acellular plasma fractions are those compositions that completely lack cells, i.e., they include no cells.

Collection of blood products comprising plasma components. Embodiments of the methods described herein include administration of blood products comprising plasma components which can be derived from donors, including human volunteers. The term, "human-derived" can refer to such products. Methods of collection of plasma comprising blood products from donors are well-known in the art. (See, e.g., AABB TECHNICAL MANUAL, (Mark A. Fung, et al., eds., 18th ed. 2014), herein incorporated by reference).

In one embodiment, donations are obtained by venipuncture. In another embodiment, the venipuncture is only a single venipuncture. In another embodiment, no saline volume replacement is employed. In a preferred embodiment, the process of plasmapheresis is used to obtain the plasma comprising blood products. Plasmapheresis can comprise the removal of a weight-adjusted volume of plasma with the return of cellular components to the donor. In the preferred embodiment, sodium citrate is used during plasmapheresis in order to prevent cell clotting. The volume of plasma collected from a donor is preferably between 690 to 880 mL after citrate administration, and preferably coordinates with the donor's weight.

C. Plasma Fractions

During the Second World War, there arose a need for a stable plasma expander which could be employed in the battlefield when soldiers lost large amounts of blood. As a result, methods of preparing freeze-dried plasma were developed. However, use of freeze-dried plasma was difficult in combat situations since reconstitution required sterile water. As an alternative, Dr. E. J. Cohn suggested that albumin could be used, and prepared a ready-to-use stable solution that could be introduced immediately for treatment of shock. (See Johan, Current Approaches to the Preparation of Plasma Fractions in (Biotechnology of Blood) 165 (Jack Goldstein ed., 1st ed. 1991)). Dr. Cohn's procedure of purifying plasma fractions utilized cold ethanol for its denaturing effect and employs changes in pH and temperature to achieve separation.

An embodiment of the methods described herein includes the administration of plasma fractions to a subject. Fractionation is the process by which certain protein subsets are separated from plasma. Fractionation technology is known in the art and relies on steps developed by Cohn et al. during the 1940s. (E. Cohn, Preparation and properties of serum and plasma proteins. IV. A system for the separation into fractions of the protein and lipoprotein components of biological tissues and fluids. 68 J Am Chem Soc 459 (1946), herein incorporated by reference). Several steps are involved in this process, each step involving specific ethanol concentrations as well as pH, temperature, and osmolality shifts which result in selective protein precipitation. Precipitates are also separated via centrifugation or precipitation. The original "Cohn fractionation process" involved separation of proteins through precipitates into five fractions, designated fraction I, fraction II+III, fraction IV-1, fraction IV-4 and fraction V. Albumin was the originally identified endpoint (fraction V) product of this process. In accordance with embodiments of the invention, each fraction (or effluent from a prior separation step) contains or potentially contains therapeutically useful protein fractions. (See Thierry Burnouf, Modern Plasma Fractionation, 21(2) Transfusion Medicine Reviews 101 (2007); Adil Denizli, Plasma fractionation: conventional and chromatographic methods for albumin purification, 4 J. Biol. & Chem. 315, (2011); and T. Brodniewicz-Proba, Human Plasma Fractionation and the Impact of New Technologies on the Use and Quality of Plasma-derived Products, 5 Blood Reviews 245 (1991), and U.S. Pat. Nos. 3,869,431, 5,110,907, 5,219,995, 7,531,513, and 8,772,461 which are herein incorporated by reference). Adjustment of the above experimental parameters can be made in order to obtain specific protein fractions.

More recently, fractionation has reached further complexity, and as such, comprises additional embodiments of the invention. This recent increase in complexity has occurred through: the introduction of chromatography resulting in isolation of new proteins from existing fractions like cryoprecipitate, cryo-poor plasma, and Cohn fractions; increasing IgG recovery by integrating chromatography and the ethanol fractionation process; and viral reduction/inactivation/removal. (Id.) In order to capture proteins at physiological pH and ionic strength, anion-exchange chromatography can be utilized. This preserves functional activity of proteins and/or protein fractions. Heparin and monoclonal antibodies are also used in affinity chromatography. Additionally, fractionation using gel filtration, fraction by salt, and fractionation by polyethylene glycol are used. (Hosseini M *Iran J Biotech*, 14(4): 213-20 (2016) herein incorporated by reference). One of ordinary skill in the art would recognize that the parameters and techniques described above may be adjusted to obtain specifically desired plasma protein-containing fractions.

Blood plasma fractionation can also be ammonium sulfate based. (See, e.g., Odunuga O O, *Biochem Compounds,* 1:3 (2013); Wingfield P T, *Curr Protoc Protein Sci*, Appx. 3 (2001), herein incorporated by reference). In addition to obtaining specific blood fractions, ammonium sulfate-based fractionation has been employed to reduce abundant proteins from plasma. (Saha S, et al., *J. Proteomics Bioinform,* 5(8) (2012), herein incorporated by reference).

In an embodiment of the invention, blood plasma is fractionated in an industrial setting. Frozen plasma is thawed at 1° C. to 4° C. Continuous refrigerated centrifugation is applied to the thawed plasma and cryoprecipitate isolated. Recovered cryoprecipitate is frozen at −30° C. or lower and stored. The cryoprecipitate-poor ("cryo-poor") plasma is immediately processed for capture (via, for example, primary chromatography) of labile coagulation factors such as factor IX complex and its components as well as protease inhibitors such as antithrombin and C1 esterase inhibitor. Serial centrifugation and precipitate isolation can be applied in subsequent steps. Such techniques are known to one of ordinary skill in the art and are described, for example, in U.S. Pat. Nos. 4,624,780, 5,219,995, 5,288,853, and U.S. patent application nos. 20140343255 and 20150343025, which disclosures are incorporated by reference in their entirety herein.

In an embodiment of the invention, the plasma fraction may comprise a plasma fraction containing a substantial concentration of albumin. In another embodiment of the invention, the plasma fraction may comprise a plasma fraction containing a substantial concentration of IgG or intravenous immune globulin (IGIV) (e.g. Gamunex-C®). In another embodiment of the invention the plasma fraction may comprise an IGIV plasma fraction, such as Gamunex-C® which has been substantially depleted of immune globulin (IgG) by methods well-known by one of ordinary skill in the art, such as for example, Protein A-mediated depletion. (See Keshishian, H., et al., Multiplexed, Quantitative Workflow for Sensitive Biomarker Discovery in Plasma Yields Novel Candidates for Early Myocardial Injury, Molecular & Cellular Proteomics, 14 at 2375-93 (2015)). In an additional embodiment, the blood plasma fraction may be one in which substantially all the clotting factors are removed in order to retain the efficacy of the fraction with reduced risk of thromboses. For example, the plasma fraction may be a plasma fraction as described in U.S. Patent No. 62/376,529 filed on Aug. 18, 2016; the disclosure of which is incorporated by reference in its entirety herein.

D. Albumin Products

To those having ordinary skill in the art, there are two general categories of Albumin Plasma Products ("APP"): plasma protein fraction ("PPF") and human albumin solution ("HAS"). PPF is derived from a process with a higher yield than HAS but has a lower minimum albumin purity than HAS (>83% for PPF and >95% for HAS). (Production of human albumin solution: a continually developing colloid, P. Matejtschuk et al., British J. of Anaesthesia 85(6): 887-95, at 888 (2000)). In some instances, PPF has albumin purity of between 83% and 95% or alternatively 83% and 96%. The albumin purity can be determined by electrophoresis or other quantifying assays such as, for example, by mass spectrometry. Additionally, some have noted that PPF has a disadvantage because of the presence of protein "contaminants" such as PKA. Id. As a consequence, PPF preparations have lost popularity as Albumin Plasma Products, and have even been delisted from certain countries'

Pharmacopoeias. Id. Contrary to these concerns, the invention makes beneficial use of these "contaminants." Besides α, β, and γ globulins, as well as the aforementioned PKA, the methods of the invention utilize additional proteins or other factors within the "contaminants" that promote processes such as cell proliferation and tissue regeneration.

Those of skill in the art will recognize that there are, or have been, several commercial sources of PPF (the "Commercial PPF Preparations.") These include Plasma-Plex™ PPF (Armour Pharmaceutical Co., Tarrytown, N.Y.), Plasmanate™ PPF (Grifols, Clayton, N.C.), Plasmatein™ (Alpha Therapeutics, Los Angeles, Calif.), and Protenate™ PPF (Baxter Labs, Inc. Deerfield, Ill.).

Those of skill in the art will also recognize that there are, or have been, several commercial sources of HAS (the "Commercial HAS Preparations.") These include Albuminar™ (CSL Behring), AlbuRx™ (CSL Behring), Albutein™ (Grifols, Clayton, N.C.), Buminate™ (Baxatla, Inc., Bannockburn, Ill.), Flexbumin™ (Baxatla, Inc., Bannockburn, Ill.), and Plasbumin™ (Grifols, Clayton, N.C.).

1. Plasma Protein Fraction (Human) (PPF)

According to the United States Food and Drug Administration ("FDA"), "Plasma Protein Fraction (Human)," or PPF, is the proper name of the product defined as "a sterile solution of protein composed of albumin and globulin, derived from human plasma." (Code of Federal Regulations "CFR" 21 CFR 640.90 which is herein incorporated by reference). PPF's source material is plasma recovered from Whole Blood prepared as prescribed in 21 CFR 640.1-640.5 (incorporated by reference herein), or Source Plasma prepared as prescribed in 21 CFR 640.60-640.76 (incorporated by reference herein).

PPF is tested to determine it meets the following standards as per 21 CFR 640.92 (incorporated by reference herein):

(a) The final product shall be a 5.0+/−0.30 percent solution of protein; and (b) The total protein in the final product shall consist of at least 83 percent albumin, and no more than 17 percent globulins. No more than 1 percent of the total protein shall be gamma globulin. The protein composition is determined by a method that has been approved for each manufacturer by the Director, Center for Biologics Evaluation and Research, Food and Drug Administration.

As used herein, "Plasma Protein Fraction" or "PPF" refers to a sterile solution of protein composed of albumin and globulin, derived from human plasma, with an albumin content of at least 83% with no more than 17% globulins (including α1, α2, β, and γ globulins) and other plasma proteins, and no more than 1% gamma globulin as determined by electrophoresis. (Hink, J. H., Jr., et al., Preparation and Properties of a Heat-Treated Human Plasma Protein Fraction, VOX SANGUINIS 2(174) (1957)). PPF can also refer to a solid form, which when suspended in solvent, has similar composition. The total globulin fraction can be determined through subtracting the albumin from the total protein. (Busher, J., Serum Albumin and Globulin, CLINICAL METHODS: THE HISTORY, PHYSICAL, AND LABORATORY EXAMINATIONS, Chapter 10, Walker H K, Hall W D, Hurst J D, eds. (1990)).

2. Albumin (Human) (HAS)

According to the FDA, "Albumin (Human)" (also referred to herein as "HAS") is the proper name of the product defined as "sterile solution of the albumin derived from human plasma." (Code of Federal Regulations "CFR" 21 CFR 640.80 which is herein incorporated by reference.) The source material for Albumin (Human) is plasma recovered from Whole Blood prepared as prescribed in 21 CFR 640.1-640.5 (incorporated by reference herein), or Source Plasma prepared as prescribed in 21 CFR 640.60-640.76 (incorporated by reference herein). Other requirements for Albumin (Human) are listed in 21 CFR 640.80-640.84 (incorporated by reference herein).

Albumin (Human) is tested to determine if it meets the following standards as per 21 CFR 640.82:

(a) Protein concentration. Final product shall conform to one of the following concentrations: 4.0+/−0.25 percent; 5.0+/−0.30 percent; 20.0+/−1.2 percent; and 25.0+/−1.5 percent solution of protein.

(b) Protein composition. At least 96 percent of the total protein in the final product shall be albumin, as determined by a method that has been approved for each manufacturer by the Director, Center for Biologics Evaluation and Research, Food and Drug Administration.

As used herein, "Albumin (Human)" or "HAS" refers to a to a sterile solution of protein composed of albumin and globulin, derived from human plasma, with an albumin content of at least 95%, with no more than 5% globulins (including α1, α2, β, and γ globulins) and other plasma proteins. HAS can also refer to a solid form, which when suspended in solvent, has similar composition. The total globulin fraction can be determined through subtracting the albumin from the total protein.

As can be recognized by one having ordinary skill in the art, PPF and HAS fractions can also be freeze-dried or in other solid form. Such preparations, with appropriate additives, can be used to make tablets, powders, granules, or capsules, for example. The solid form can be formulated into preparations for injection by dissolving, suspending or emulsifying them in an aqueous or non-aqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

E. Clotting Factor-Reduced Fractions

Another embodiment of the invention uses a blood plasma fraction from which substantially all of the clotting factors are removed in order to retain the efficacy of the fraction with reduced risk of thromboses. Conveniently, the blood product can be derived from a young donor or pool of young donors and can be rendered devoid of IgM in order to provide a young blood product that is ABO compatible. Currently, plasma that is transfused is matched for ABO blood type, as the presence of naturally occurring antibodies to the A and B antigens can result in transfusion reactions. IgM appears to be responsible for transfusion reactions when patients are given plasma that is not ABO matched. Removal of IgM from blood products or fractions helps eliminate transfusion reactions in subjects who are administered the blood products and blood plasma fractions of the invention.

Accordingly, in one embodiment, the invention is directed to a method of treating a subject suffering from an unwanted condition associated with any of the following a liver disorder or liver failure. The method comprises: administering to the subject a blood product or blood fraction derived from whole-blood from an individual or pool of individuals, wherein the blood product or blood fraction is substantially devoid of (a) at least one clotting factor and/or (b) IgM. In some embodiments, the individual(s) from whom the blood product or blood fraction is derived are young individuals. In some embodiments, the blood product is substantially devoid of at least one clotting factor and IgM. In certain embodiments, the blood product is substantially devoid of fibrinogen (Factor I). In additional embodiments, the blood product substantially lacks erythrocytes and/or leukocytes. In further embodiments, the blood product is substantially acellular. In other embodiments, the blood product is derived from plasma. Such embodiments of the invention are further supported by U.S. Patent Application No. 62/376,529 filed on Aug. 18, 2016, which is incorporated by reference in its entirety herein.

F. Protein-Enriched Plasma Protein Products Treatment

Additional embodiments of the invention use plasma fractions with reduced albumin concentration compared to PPF, but with increased amounts of globulins and other plasma proteins (what have been referred to by some as "contaminants"). The embodiments, as with PPF, HAS, Effluent I, and Effluent II/III are all effectively devoid of clotting factors. Such plasma fractions are hereinafter referred to as "protein-enriched plasma protein products." For example, an embodiment of the invention may use a protein-enriched plasma protein product comprised of 82% albumin and 18% α, β, and γ globulins and other plasma proteins. Another embodiment of the invention may use a protein-enriched plasma protein product comprised of 81% albumin and 19% of α, β, and γ globulins and/or other plasma proteins. Another embodiment of the invention may use a protein-enriched plasma protein product comprised of 80% albumin and 20% of α, β, and γ globulins and/or other plasma proteins. Additional embodiments of the invention may use protein-enriched plasma protein products comprised of 70-79% albumin and a corresponding 21-30% of α, β, and γ globulins and other plasma proteins. Additional embodiments of the invention may use protein-enriched plasma protein products comprised of 60-69% albumin and a corresponding 31-40% of α, β, and γ globulins and other plasma proteins. Additional embodiments of the invention may use protein-enriched plasma protein products comprised of 50-59% albumin and a corresponding 41-50% of α, β, and γ globulins and other plasma proteins. Additional embodiments of the invention may use protein-enriched plasma protein products comprised of 40-49% albumin and a corresponding 51-60% of α, β, and γ globulins and other plasma proteins. Additional embodiments of the invention may use protein-enriched plasma protein products comprised of 30-39% albumin and a corresponding 61-70% of α, β, and γ globulins and other plasma proteins. Additional embodiments of the invention may use protein-enriched plasma protein products comprised of 20-29% albumin and a corresponding 71-80% of α, β, and γ globulins and other plasma proteins. Additional embodiments of the invention may use protein-enriched plasma protein products comprised of 10-19% albumin and a corresponding 81-90% of α, β, and γ globulins and other plasma proteins. Additional embodiments of the invention may use protein-enriched plasma protein products comprised of 1-9% albumin and a corresponding 91-99% of α, β, and γ globulins and other plasma proteins. A further embodiment of the invention may use protein-enriched plasma protein products comprised of 0% albumin and 100% of α, β, and γ globulins and other plasma proteins.

Embodiments of the invention described above may also have total gamma globulin concentrations of 1-5%.

The specific concentrations of proteins in a plasma fraction may be determined using techniques well-known to a person having ordinary skill in the relevant art. By way of example, and not limitation, such techniques include electrophoresis, mass spectrometry, ELISA analysis, and Western blot analysis.

G. Preparation of Plasma Fractions

Methods of preparing PPF and other plasma fractions are well-known to those having ordinary skill in the art. An embodiment of the invention allows for blood used in the preparation of human plasma protein fraction to be collected in flasks with citrate or anticoagulant citrate dextrose solution (or other anticoagulant) for inhibition of coagulation, with further separation of Fractions I, II+III, IV, and PPF as per the method disclosed in Hink et al. (See Hink, J. H., Jr., et al., Preparation and Properties of a Heat-Treated Human Plasma Protein Fraction, VOX SANGUINIS 2(174) (1957), herein incorporated by reference.) According to this method, the mixture can be collected to 2-8° C. The plasma can then subsequently be separated by centrifugation at 7° C., removed, and stored at −20° C. The plasma can then be thawed at 37° C. and fractionated, preferably within eight hours after removal from −20° C. storage.

Plasma can be separated from Fraction I using 8% ethanol at pH 7.2 and a temperature at −2 to −2.5° C. with protein concentration of 5.1 to 5.6 percent. Cold 53.3 percent ethanol (176 mL/L of plasma) with acetate buffer (200 mL 4M sodium acetate, 230 mL glacial acetic acid quantum satis to 1 L with $H_2O$) can be added using jets at a rate, for example, of 450 mL/minute during the lowering the plasma temperature to −2° C. Fraction I can be separated and removed from the effluent (Effluent I) through ultracentrifugation. Fibrinogen can be obtained from Fraction I as per methods well-known to those having ordinary skill in the art.

Fraction II+III can be separated from Effluent I through adjustment of the effluent to 21 percent ethanol at pH 6.8, temperature at −6° C., with protein concentration of 4.3 percent. Cold 95 percent ethanol (176 mL/L of Effluent I) with 10 M acetic acid used for pH adjustment can be added using jets at a rate, for example, of 500 mL/minute during the lowering of the temperature of Effluent I to −6° C. The resulting precipitate (Fraction II+III) can be removed by centrifugation at −6° C. Gamma globulin can be obtained from Fraction II+III using methods well-known to those having ordinary skill in the art.

Fraction IV-1 can be separated from Effluent II+III ("Effluent II/III") through adjustment of the effluent to 19 percent ethanol at pH 5.2, temperature at −6° C., and protein concentration of 3 percent. $H_2O$ and 10 M acetic acid used for pH adjustment can be added using jets while maintaining Effluent II/III at −6° C. for 6 hours. Precipitated Fraction IV-1 can be settled at −6° C. for 6 hours and subsequently separated from the effluent by centrifugation at the same temperature. Stable plasma protein fraction can be recovered from Effluent IV-1 through adjustment of the ethanol concentration to 30 percent at pH 4.65, temperature −7° C. and protein concentration of 2.5 percent. This can be accomplished by adjusting the pH of Effluent IV-1 with cold acid-alcohol (two parts 2 M acetic acid and one-part 95 percent ethanol). While maintaining a temperature of −7° C., to every liter of adjusted Effluent IV-1 170 mL cold ethanol (95%) is added. Proteins that precipitate can be allowed to settle for 36 hours and subsequently removed by centrifugation at −7° C. Fraction IV-4 paste can also be attained using the Cohn fractionation process. Indeed, Fraction IV-4 and its manufacturing process has been described previously (Schopfer L M, et al., *PLoS ONE*, 14(1):e0209795 (2018) and herein incorporated by reference in its entirety) (Schopfer L M, et al., *PLoS ONE*, 14(1):e0209795 (2018), and Bertolini J, Goss N, Curlin J eds., PRODUCTION OF PLASMA PROTEINS FOR THERAPEUTIC USE, 16.4: 231:232 (2013) herein incorporated by reference in their entirety).

The recovered proteins (stable plasma protein fraction) can be dried (e.g. by freeze drying) to remove alcohol and $H_2O$. The resulting dried powder can be dissolved in sterile distilled water, for example using 15 liters of water/kg of powder, with the solution adjusted to pH 7.0 with 1 M NaOH. A final concentration of 5 percent protein can be achieved by adding sterile distilled water containing sodium acetyl tryptophanate, sodium caprylate, and NaCl, adjusting to final concentrations of 0.004 M acetyl tryptophanate, 0.004 M caprylate, and 0.112 M sodium. Finally, the solution can be filtered at 10° C. to obtain a clear solution and subsequently heat-treated for inactivation of pathogens at 60° C. for at least 10 hours.

One having ordinary skill in the art would recognize that each of the different fractions, effluents, or pastes thereof described above could be used with the methods of the invention to treat conditions such as liver disorders or liver failure. For example, and not by way of limitation, Effluents I or Effluent II/III may be utilized to treat conditions such as a liver disorder or liver failure. and are embodiments of the invention. A further example is that Fraction I paste, Fraction II+III paste, Fraction IV-1 paste, Fraction IV-4 paste and/or Fraction V paste or suspensions thereof may be utilized to treat conditions such as a liver disorder or liver failure. and are embodiments of the invention.

The preceding methods of preparing plasma fractions and plasma protein fraction (PPF) are only exemplary and involve merely embodiments of the invention. One having ordinary skill in the art would recognize that these methods can vary. For example, pH, temperature, and ethanol concentration, among other things can be adjusted to produce different variations of plasma fractions and plasma protein fraction in the different embodiments and methods of the invention. In another example, additional embodiments of the invention contemplate the use of nanofiltration for the removal/inactivation of pathogens from plasma fractions and plasma protein fraction.

An additional embodiment of the invention contemplates methods and composition using and/or comprising additional plasma fractions. For example, the invention, among other things, contemplates that specific concentrations of albumin are not critical for treating conditions associated with a liver disorder or liver failure. Hence, fractions with reduced albumin concentration, such as those fractions having below 83% albumin, are contemplated by the invention.

H. Treatment

Aspects of the methods of the inventions described herein include treatment of a subject with a plasma comprising blood product, such as a blood plasma fraction, e.g., as described above. An embodiment includes treatment of a human subject with a plasma comprising blood product. One of skill in the art would recognize that methods of treatment of subjects with plasma comprising blood products are recognized in the art. By way of example, and not limitation, one embodiment of the methods of the inventions described herein is comprised of administering plasma fraction or fresh frozen plasma to a subject for treatment of liver-related disorders such as acute failure or chronic failure. Further embodiments of the invention include wherein the acute liver failure is associated with infectious disease such as hepatitis B or C, overuse of drugs or toxins (e.g. acetaminophen, isoniazid), and metabolic or vascular disorders like autoimmune hepatitis and Wilson disease. Additional embodiments of the invention include wherein the chronic liver failure is associated with viral infections, alcohol abuse, NAFLD (caused by obesity, high cholesterol and triglycerides, and high blood pressure), autoimmune disorders, blocked or damaged tubes such as bile ducts from the liver to the intestine, exposure to toxins or certain medicines, parasites, heart failure resulting in buildup of blood in the liver.

Further embodiments of the invention include liver disorders or liver failure associated with genetic diseases including by way of example and not limitation: alpha-1 antitrypsin deficiency; bile acid synthesis disorders (Wilson disease, progressive familial intrahepatic cholestasis type 3); disorders of carbohydrate metabolism (Hereditary fructose intolerance, glycogen storage disease type IV); disorders of amino acids metabolism (tyrosinemia type I); urea cycle disorders (argininosuccinate lyase deficiency, citrin deficiency—CTLN2, NICCD); disorders of lipid metabolism (cholesteryl ester storage disease); cystic fibrosis; hemochromatosis; Alstrom syndrome; and congenital hepatic fibrosis. (Scorza M, et al., *Int'l J Hepatology,* 2014, Article ID 713754 (2014)).

Additional embodiments of the invention include liver disorders or liver failure associated with infectious agents such as, by way of example and not limitation: viruses (Epstein Barr virus, cytomegalovirus, Herpes Simplex Virus and other Herpes viruses, yellow fever, dengue, Hepatitis B and C); bacteria (typhoid fever, *Mycobacterium tuberculosis*, brucellosis, Q fever, leptospirosis, spirochetes—syphilis, *Borrelia*); parasites (schistosomiasis, malaria); fungi (candida). (Talwani R, et al., *Clin Liver Dis.,* 15(1):111-30 (2011)).

Additional embodiments of the invention include liver disorders or liver failure associated with drugs or toxic substances such as, by way of example and not limitation: acetaminophen, isoniazid, and drugs metabolized by the liver.

Further embodiments of the invention include liver disorders wherein the liver is resected partially or completely. Additional embodiments include liver disorders wherein a donor liver is transplanted into the subject suffering from the liver disorder. Additional embodiments include administration to the subject of the therapeutic agent such as plasma comprising blood products or plasma fractions pre-, peri-, and/or post-operatively.

In one embodiment, the plasma comprising blood product is administered immediately, e.g., within about 12-48 hours of collection from a donor, to the individual suffering from a condition associated with liver disorders or liver failure. In such instances, the product may be stored under refrigeration, e.g., 0-10° C. In another embodiment, fresh frozen plasma is one that has been stored frozen (cryopreserved) at −18° C. or colder. Prior to administration, the fresh frozen plasma is thawed and once thawed, administered to a subject 60-75 minutes after the thawing process has begun. Each subject preferably receives a single unit of fresh frozen plasma (200-250 mL), the fresh frozen plasma preferably derived from donors of a pre-determined age range. In one embodiment of the invention, the fresh frozen plasma is donated by (derived from) young individuals. In another embodiment of the invention, the fresh frozen plasma is donated by (derived from) donors of the same gender. In another embodiment of the invention, the fresh frozen plasma is donated by (derived from) donors of the age range between 18-22 years old.

In an embodiment of the invention, the plasma comprising blood products are screened after donation by blood type. In another embodiment of the invention, the plasma comprising blood products are screened for infectious disease agents such as HIV I & II, HBV, HCV, HTLV I & II, anti-HBc per the requirements of 21 CFR 640.33 and recommendations contained in FDA guidance documents.

In yet another embodiment of the invention, the subject is treated with a Plasma Fraction. In an embodiment of the invention, the plasma fraction is a PPF, HAS, Fraction IV-1, Fraction IV-1 paste, Fraction IV-4 or Fraction IV-4 paste. In a further embodiment of the invention, the plasma fraction is one of the Commercial PPF Preparations of the Commercial HAS Preparations. In another embodiment of the invention the plasma fraction is a PPF, HAS, Fraction IV-4 or Fraction IV-4 paste derived from a pool of individuals of a specific age range, such as young individuals, or is a modified PPF, HAS, Fraction IV-4 or Fraction IV-4 paste fraction which has been subjected to additional fractionation or processing (e.g. PPF, HAS, Fraction IV-1, Fraction IV-1 paste, Fraction IV-4 or Fraction IV-4 paste with one or more specific proteins partially or substantially removed). In another embodiment of the invention, the plasma fraction is an IGIV plasma fraction which has been substantially depleted of immune globulin (IgG). A blood fraction which is "substantially depleted" or which has specific proteins "substantially removed," such as IgG, refers to a blood fraction containing less than about 50% of the amount that occurs in the reference product or whole blood plasma, such as less than 45%, 40%, 35%, 30%, 25%, 20%, 15%, 5%, 4%, 3%, 2%, 1%, 0.5%, 0.25%, 0.1%, undetectable levels, or any integer between these values, as measured using standard assays well known in the art.

I. Administration

Aspects of the methods of the inventions described herein include treatment of a subject with a plasma comprising blood product, such as a blood plasma or Plasma Fraction, e.g., as described above. An embodiment includes treatment of a human subject with a plasma comprising blood product. One of skill in the art would recognize that methods of treatment of subjects with plasma comprising blood products are recognized in the art. By way of example, and not limitation, one embodiment of the methods of the inventions described herein is comprised of administering fresh frozen plasma to a subject for treatment of conditions such as liver disorders or liver failure In one embodiment, the plasma comprising blood product is administered immediately, e.g., within about 12-48 hours of collection from a donor, to the individual suffering from an unwanted condition such as a liver disorder or failure. In such instances, the product may be stored under refrigeration, e.g., 0-10° C. In another embodiment, fresh frozen plasma is one that has been stored frozen (cryopreserved) at −18° C. or colder. Prior to administration, the fresh frozen plasma is thawed and once thawed, administered to a subject 60-75 minutes after the thawing process has begun. Each subject preferably receives a single unit of fresh frozen plasma (200-250 mL), the fresh frozen plasma preferably derived from donors of a pre-determined age range. In one embodiment of the invention, the fresh frozen plasma is donated by (derived from) young individuals. In another embodiment of the invention, the fresh frozen plasma is donated by (derived from) donors of the same gender. In another embodiment of the invention, the fresh frozen plasma is donated by (derived from) donors of the age range between 18-22 years old.

In an embodiment of the invention, the plasma comprising blood products are screened after donation by blood type. In another embodiment of the invention, the plasma comprising blood products are screened for infectious disease agents such as HIV I & II, HBV, HCV, HTLV I & II, anti-HBc per the requirements of 21 CFR 640.33 and recommendations contained in FDA guidance documents.

In yet another embodiment of the invention, the subject is treated with a Plasma Fraction. In an embodiment of the invention, the plasma fraction is PPF or HAS. In a further embodiment of the invention, the plasma fraction is one of the Commercial PPF Preparations or the Commercial HAS Preparations. In another embodiment of the invention the plasma fraction is a PPF or HAS derived from a pool of individuals of a specific age range, such as young individuals, or is a modified PPF or HAS fraction which has been subjected to additional fractionation or processing (e.g. PPF or HAS with one or more specific proteins partially or substantially removed). In another embodiment of the invention, the plasma fraction is an IGIV plasma fraction which has been substantially depleted of immune globulin (IgG). A blood fraction which is "substantially depleted" or which has specific proteins "substantially removed," such as IgG, refers to a blood fraction containing less than about 50% of the amount that occurs in the reference product or whole blood plasma, such as less than 45%, 40%, 35%, 30%, 25%, 20%, 15%, 5%, 4%, 3%, 2%, 1%, 0.5%, 0.25%, 0.1%, undetectable levels, or any integer between these values, as measured using standard assays well known in the art.

An embodiment of the invention includes treating a subject suffering from a condition such as such as a liver disorder or liver failure by administering to the subject an effective amount of blood plasma or Plasma Fraction. Another embodiment of the invention includes administering the effective amount of blood plasma or Plasma Fraction and subsequently monitoring the subject for improved liver function, liver regeneration, the presence of markers, decreased pain, or decreased inflammation. Another embodiment of the invention includes treating a subject suffering from a condition associated such as such as a liver disorder or liver failure by administering to the subject an effective amount of blood plasma or Plasma Fraction wherein the blood plasma or Plasma Fraction is administered in a manner resulting in improved liver function, liver regeneration, the presence of markers, decreased pain, or decreased inflammation after the mean or median half-life of the blood plasma proteins or Plasma Fraction proteins been reached, relative to the most recent administered dose (referred to as "Pulsed Dosing" or "Pulse Dosed" herein) (See U.S. patent application Ser. Nos. 15/499,697 and 62/701, 411, which are herein incorporated by reference in their entirety). Another embodiment of the invention includes administering the blood plasma or Plasma Fraction via a dosing regimen of at least two consecutive days and monitoring the subject for improved liver function or HSC marker levels at least 3 days after the date of last administration. A further embodiment of the invention includes administering the blood plasma or Plasma Fraction via a dosing regimen of at least 3, 4, 5, 6, 7, 8, 9, 10, 11, 12, 13, or 14 consecutive days and monitoring the subject for improved liver function, liver regeneration, the presence of markers, decreased pain, or decreased inflammation at least 3 days after the date of last administration. Yet another embodiment of the invention includes administering the blood plasma or Plasma Fraction via a dosing regimen of at least 2 consecutive days and after the date of last administration, monitoring for functional improvement of the liver, the presence of markers, decreased pain, or decreased inflammation beyond when the average half-life of the proteins in the blood plasma or Plasma Fraction has been reached. Another embodiment of the invention includes administering the blood plasma or Plasma Fraction via a dosing regimen of 2 to 14 non-consecutive days wherein each gap between doses may be between 0-3 days each.

In some instances, Pulsed Dosing in accordance with the invention includes administration of a first set of doses, e.g., as described above, followed by a period of no dosing, e.g., a "dosing-free period", which in turn is followed by administration of another dose or set of doses. The duration of this "dosing-free" period, may vary, but in some embodiments, is 7 days or longer, such as 10 days or longer, including 14 days or longer, wherein some instances the dosing-free period ranges from 15 to 365 days, such as 30 to 90 days and including 30 to 60 days. As such, embodiments of the methods include non-chronic (i.e., non-continuous) dosing, e.g., non-chronic administration of a blood plasma product. In some embodiments, the pattern of Pulsed Dosing followed by a dosing-free period is repeated for a number of times, as desired, where in some instances this pattern is continued for 1 year or longer, such as 2 years or longer, up to and including the life of the subject. Another embodiment of the invention includes administering the blood plasma or Plasma Fraction via a dosing regimen of 5 consecutive days, with a dosing-free period of 2-3 days, followed by administration for 2-14 consecutive days.

A further embodiment of the invention includes liver disorders wherein the liver is resected partially or completely. Additional embodiments include liver disorders wherein a donor liver is transplanted into the subject suffering from the liver disorder. Additional embodiments include administration to the subject of the therapeutic agent such as plasma comprising blood products or plasma fractions pre-, peri-, and/or post-operatively. Methods of resecting and transplanting a liver are well known in the art.

Biochemically, by an "effective amount" or "effective dose" of active agent is meant an amount of active agent that will inhibit, antagonize, decrease, reduce, or suppress by about 20% or more, e.g., by 30% or more, by 40% or more, or by 50% or more, in some instances by 60% or more, by 70% or more, by 80% or more, or by 90% or more, in some cases by about 100%, i.e., to negligible amounts, and in some instances, reverse unwanted conditions such as such as a liver disorder or liver failure.

J. Plasma Protein Fraction

In practicing methods of the invention, a plasma fraction is administered to the subject. In an embodiment, the plasma fraction is plasma protein fraction (PPF). In additional embodiments, the PPF is selected from the Commercial PPF Preparations.

In another embodiment, the PPF is comprised of 88% normal human albumin, 12% alpha and beta globulins and not more than 1% gamma globulin as determined by electrophoresis. Further embodiments of this embodiment used in practicing methods of the invention include, for example, the embodiment as a 5% solution of PPF buffered with sodium carbonate and stabilized with 0.004 M sodium caprylate and 0.004 M acetyltryptophan. Additional formulations, including those modifying the percentage of PPF (e.g. about 1% to about 10%, about 10% to about 20%, about 20% to 25%, about 25% to 30%) in solution as well as the concentrations of solvent and stabilizers may be utilized in practicing methods of the invention.

K. Plasma Fractions of Specific Donor Age

Additional embodiments of the invention include administering a plasma protein fraction derived from the plasma of individuals of certain age ranges. An embodiment includes administering PPF or HAS which have been derived from the plasma of young individuals. In another embodiment of the invention the young individuals are of a single specific age or a specific age range. In yet another embodiment, the average age of the donors is less than that of the subject or less than the average age of the subjects being treated.

Certain embodiments of the invention include pooling blood or blood plasma from individuals of specific age ranges and fractionating the blood plasma as described above to attain a plasma protein fraction product such as PPF or HAS. In an alternate embodiment of the invention, the plasma protein fraction or specific plasma protein fraction is attained from specific individuals fitting a specified age range.

L. Indications

An embodiment of the invention is using plasma fractions and products of blood plasma fractionation to administer to a subject diagnosed with a liver disorder or liver failure that could benefit from improved liver proliferation or regeneration. A further embodiment of the invention includes when said disease is associated with: acute liver failure, chronic liver failure or acute-on-chronic liver failure. Acute-on-chronic liver failure occurs in patients with relatively stable chronic liver disease but suddenly turns into acute liver failure. This usually results in a very high mortality rate. Another embodiment of the invention is wherein the acute failure is associated with infectious disease such as hepatitis B or C, overuse of drugs or toxins (e.g. acetaminophen, isoniazid), and metabolic or vascular disorders like autoimmune hepatitis and Wilson disease. Additional embodiments of the invention include wherein the chronic liver failure is associated with viral infections, alcohol abuse, NAFLD (caused by obesity, high cholesterol and triglycerides, and high blood pressure), autoimmune disorders, blocked or damaged tubes such as bile ducts from the liver to the intestine, exposure to toxins or certain medicines, parasites, heart failure resulting in buildup of blood in the liver.

Further embodiments of the invention include liver disorders or liver failure associated with genetic diseases including by way of example and not limitation: alpha-1 antitrypsin deficiency; bile acid synthesis disorders (Wilson disease, progressive familial intrahepatic cholestasis type 3); disorders of carbohydrate metabolism (Hereditary fructose intolerance, glycogen storage disease type IV); disorders of amino acids metabolism (tyrosinemia type I); urea cycle disorders (argininosuccinate lyase deficiency, citrin deficiency—CTLN2, NICCD); disorders of lipid metabolism (cholesteryl ester storage disease); cystic fibrosis; hemochromatosis; Alstrom syndrome; and congenital hepatic fibrosis. (Scorza M, et al., *Int'l J Hepatology,* 2014, Article ID 713754 (2014)).

Additional embodiments of the invention include liver disorders or liver failure associated with infectious agents such as, by way of example and not limitation: viruses (Epstein Barr virus, cytomegalovirus, Herpes Simplex Virus and other Herpes viruses, yellow fever, dengue, Hepatitis B and C); bacteria (typhoid fever, *Mycobacterium tuberculosis*, brucellosis, Q fever, leptospirosis, spirochetes—syphilis, *Borrelia*); parasites (schistosomiasis, malaria); fungi (candida). (Talwani R, et al., *Clin Liver Dis.*, 15(1):111-30 (2011)).

Additional embodiments of the invention include liver disorders or liver failure associated with drugs or toxic substances such as, by way of example and not limitation: acetaminophen, isoniazid, and drugs metabolized by the liver.

Further embodiments of the invention include liver disorders wherein the liver is resected partially Additional embodiments include liver disorders wherein a donor liver is transplanted into the subject suffering from the liver disorder. Additional embodiments include administration to the subject of the therapeutic agent such as plasma comprising blood products or plasma fractions pre-, peri-, and/or postoperatively.

M. Reagents, Devices, and Kits

Also provided are reagents, devices, and kits thereof for practicing one or more of the above-described methods. The subject reagents, devices, and kits thereof may vary greatly.

Reagents and devices of interest include those mentioned above with respect to the methods of preparing plasma-comprising blood product for transfusion into a subject in need hereof, for example, anti-coagulants, cryopreservatives, buffers, isotonic solutions, etc.

Kits may also comprise blood collection bags, tubing, needles, centrifugation tubes, and the like. In yet other embodiments, kits as described herein include two or more containers of blood plasma product such as plasma protein fraction, such as three or more, four or more, five or more, including six or more containers of blood plasma product. In some instances, the number of distinct containers of blood plasma product in the kit may be 9 or more, 12 or more, 15 or more, 18 or more, 21 or more, 24 or more 30 or more, including 36 or more, e.g., 48 or more. Each container may have associated therewith identifying information which includes various data about the blood plasma product contained therein, which identifying information may include one or more of the age of the donor of the blood plasma product, processing details regarding the blood plasma product, e.g., whether the plasma product was processed to remove proteins above an average molecule weight (such as described above), blood type details, etc. In some instances, each container in the kit includes identifying information about the blood plasma contained therein, and the identifying information includes information about the donor age of the blood plasma product, e.g., the identifying information provides confirming age-related data of the blood plasma product donor (where such identifying information may be the age of the donor at the time of harvest). In some instances, each container of the kit contains a blood plasma product from a donor of substantially the same age, i.e., all of the containers include product from donors that are substantially the same, if not the same, age. By substantially the same age is meant that the various donors from which the blood plasma products of the kits are obtained differ in each, in some instances, by 5 years or less, such as 4 years or less, e.g., 3 years or less, including 2 years or less, such as 1 year or less, e.g., 9 months or less, 6 months or less, 3 months or less, including 1 month or less. The identifying information can be present on any convenient component of the container, such as a label, an RFID chip, etc. The identifying information may be human readable, computer readable, etc., as desired. The containers may have any convenient configuration. While the volume of the containers may vary, in some instances the volumes range from 10 ml to 5000 mL, such as 25 mL to 2500 mL, e.g., 50 ml to 1000 mL, including 100 mL to 500 mL. The containers may be rigid or flexible, and may be fabricated from any convenient material, e.g., polymeric materials, including medical grade plastic materials. In some instances, the containers have a bag or pouch configuration. In addition to the containers, such kits may further include administration devices, e.g., as described above. The components of such kits may be provided in any suitable packaging, e.g., a box or analogous structure, configured to hold the containers and other kit components.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, portable flash drive, etc., on which the information has been recorded. Yet another means that may be present is a website address which may be used via the internet to access the information at a removed site. Any convenient means may be present in the kits.

N. Experimental Examples

1. Example 1 a) PPF1-Induced Functional Recovery of 20-Month-Old C57BL/6 Mouse Livers After 70% Partial Hepatectomy Male C57BL/6J mice (The Jackson Laboratory, Sacramento, Calif.) aged for 20 months were used. All mice were individually housed under specific pathogen-free conditions under a 12-hour light, 12-hour dark cycle, and all animal handling and use was in accordance with Institutional Animal Care and Use Committee approved standard guidelines. Animals were fed with 60% high fat diet (Bio-Serv F3282) for 7-8 weeks and randomized into vehicle vs PPF1 treated groups according to their body weights and ALT levels after the diet to ensure the same average body weight and serum ALT levels between groups. Surgery was performed with minor modifications as described previously (Nevzorova, Y., et al., *Lab. Anim.* 49, 81-88 (2015)). The resected liver (left and medial lobes) were taken as pre-surgery controls whereas remnant liver (caudal and right) were harvested 48 hour after surgery. Twenty-four (24) hours post-surgery, EdU (stock at 2.5 mg/mL in saline) was injected I.P. at 30 mg/kg of body weight. Forty-six (46) hours post-surgery, BrdU (stock at 10 mg/mL in saline) was injected I.P. at 30 mg/kg of body weight. At 48 h post-surgery, all animals were weighed, and remnant livers (medial and caudal) and serum were collected for ALT analysis.

Commercially available PPF ("PPF1") such as those Commercial PPF Preparations described above in 5% solution were stored at 4° C. PPF1 is a PPF with approximately 88% normal human albumin (in relation to total protein), 12% alpha and beta globulins, and no more than 1% gamma globulin as determined by electrophoresis. Except where noted, PPF1 is administered in the examples herein using a 5% solution (w/v/, 50 g/L).

For qPCR analysis, RNA was extracted from resected or remnant livers that were powderized with liquid nitrogen and a mortar/pestle. Extraction was subsequently carried out with Trizol (Ambion/Fisher 15-596-018) and RNeasy Mini Kit (Qiagen 74106). cDNA was amplified with iScript Reverse Transcription Supermix (Bio-Rad 1030). QPCR was amplified with SsoAdvanced Universal SYBR green master mix (Bio-Rad 1725272) and performed with Quant Studio 6 Flex (Applied Biosystem). Gene expression was normalized to RPS18 (ribosomal protein s18).

For immunostaining, 12-micron thick frozen liver sections embedded in OCT compound (Sakura 4583) were used for immunofluorescent staining. Antigen retrieval was performed with citrate buffer (Sigma C9999) at 95° C. for 30 minutes. For EdU labeling, Click-IT Plus EdU Alexa Fluor 555 was used (Fisher C10638). Hoechst 33342 was used at 1 to 100,000 in ddH2O for 3 minutes to label nuclei (Fisher H3570). Oil-red O staining was performed to visualize triglyceride accumulation in liver. Briefly, frozen liver sections were immersed in 0.375% Oil-red O in isopropyl alcohol for 5 minutes. The sections were rinsed under running tap water for 30 minutes and mounted with Prolong gold antifade reagent (Invitrogen P36934).

Figure 1:
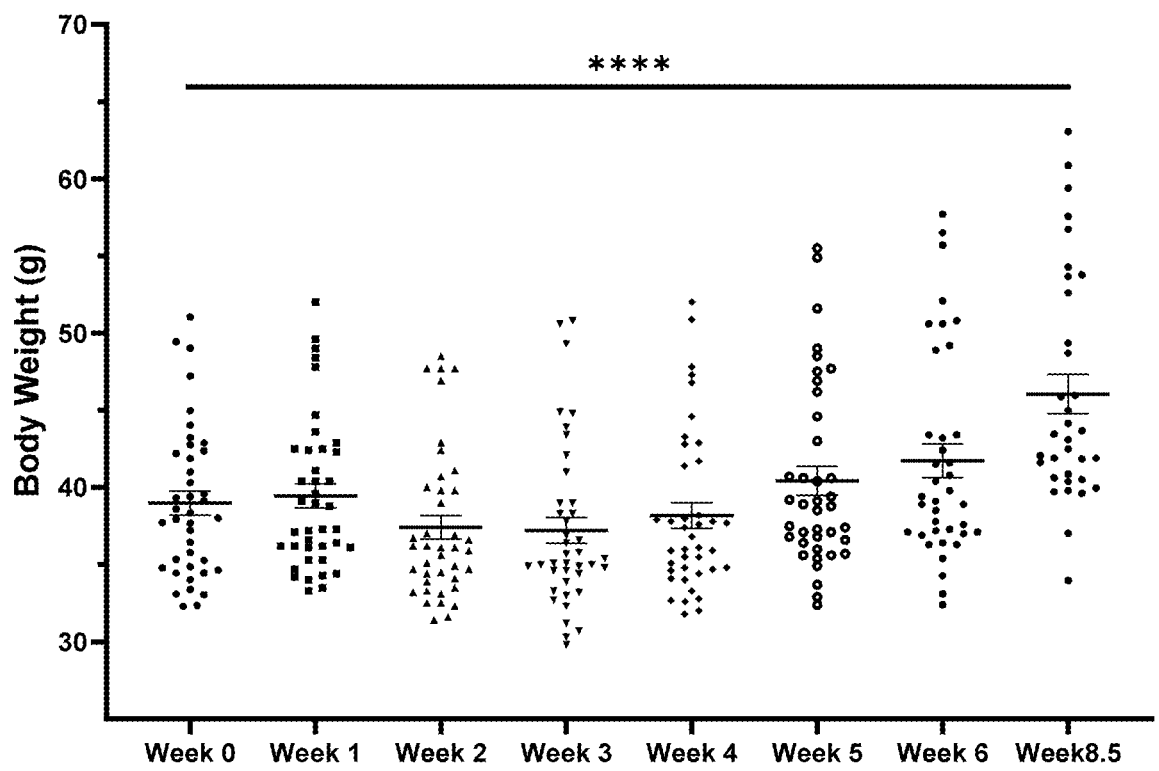
FIG. 1 is a graph showing the progression of body weight of 20-month-old C57BL/6 mice placed on a high fat diet ("HFD"). After 8.5 weeks on HFD, the mice developed significant weight gain.

FIG. 1 is a graph showing the progression of body weight of 20-month-old C57BL/6 mice placed on a high fat diet ("HFD"). After 8.5 weeks on HFD, the mice developed significant weight gain. Mean±SEM, ****$p<0.0001$ ordinary one-way ANOVA.

Figure 2:
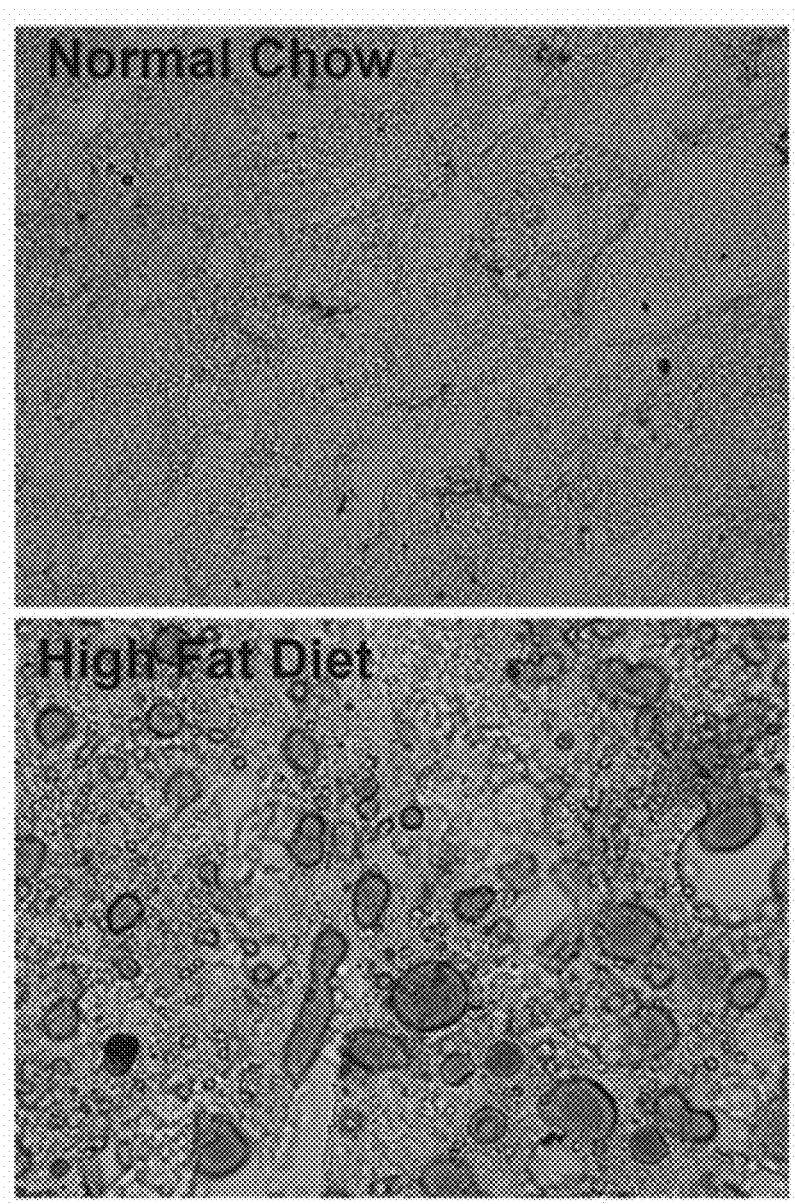
FIG. 2 is an oil-red-o stain of livers from mice as described in FIG. 1. Mice on HFD developed fatty livers as compared to those mice on a normal diet ("normal chow").

FIG. 2 is an oil-red-o stain of livers from mice as described in FIG. 1. Mice on HFD developed fatty livers as compared to those mice on a normal diet ("normal chow").

FIG. 3 shows the design of this experiment to evaluate effects of PPF1 on 20-month-old C57BL/6 mice on a high fat diet as described above.

FIG. 4 identifies the resected and remnant lobes resulting from the 70% hepatectomy in mice treated as described in FIG. 3.

FIG. 5 shows results from the determination of liver weight to body weight ratio in vehicle and PPF1-treated resected livers hepatectomy from mice treated as described in FIG. 3.

FIG. 6 shows liver weights in vehicle and PPF1-treated resected livers from mice treated as described in FIG. 3.

FIG. 7 is a graph showing serum ALT levels is normal and unaffected in PPF1-treated mice on HFD before hepatectomy. ALT levels are considered normal when they are under 50-60 units per liter. (See, e.g., Mazzaccara C, et al., *PLoS ONE*, 3(11):e3772 (2008)).

FIG. 8 shows results from the determination of liver weight to body weight ratio in vehicle and PPF1-treated mice with remnant livers 48 hours after hepatectomy as described in FIG. 3. In comparison to vehicle treated animals, PPF1 treated animals had a significant increase in liver weight 48 hours post-hepatectomy. Mean±SEM, **$p<0.001$ with Unpaired T test with Whitney correction.

FIG. 9 shows liver weights in vehicle and PPF1-treated mice with remnant livers 48 hours after hepatectomy as described in FIG. 3. In comparison to vehicle treated animals, PPF1 treated animals had a significant increase in liver weight 48 hours post-hepatectomy. Mean±SEM, *$p<0.05$ with Unpaired T test with Whitney correction.

FIG. 10 shows results of serum ALT levels in vehicle and PPF1-treated mice with remnant livers 48 hours after hepatectomy as described in FIG. 3. In comparison to vehicle treated animals, PPF1 treated animals have a significant decrease in serum ALT levels 48 hours post-hepatectomy indicating that the extent of liver damage was also significantly decreased in animals treated with PPF1. Mean±SEM, **$p<0.001$ with Unpaired T test with Whitney correction.

In contrast, differences in resected liver weights, liver weight/body weight ratios, and ALT levels failed to reach levels of significance between vehicle treated and PPF1 treated animals.

FIG. 11 reports cell proliferation rates after hepatectomy. EdU was delivered at 24-hours post-hepatectomy and the proliferation rates were traced by Click-it labeling of EdU-positive cells. PPF1 significantly increased the EdU-positive number of cells per field compared to vehicle-treated animals in remnant livers.

FIG. 12 reports cell proliferation at 48 hours post-hepatectomy as measured by the number of Ki67-positive cells per field. PPF1 significantly increased Ki67-positive number of cells per field compared to vehicle-treated animals in remnant livers.

FIG. 13 reports cellular proliferation rates in remnant livers by qPCR gene expression. Relative expression of cell cycle marker Cycle B1 is shown. In remnant liver sections, Cyclin B1 expression was significantly up-regulated in PPF1-treated mice versus vehicle-treated mice. Mean±SEM, *$p<0.05$ with Unpaired T test with Whitney.

FIG. 14A through FIG. 14D report qPCR expression of several markers in resected livers by. Relative expression of cell cycle markers Cycle B1 (FIG. 14A), Cyclin A2 (FIG. 14B), and Ki67 (FIG. 14C) are shown. In resected liver sections, which were removed during hepatectomy as pre-surgery controls, PPF1 surprisingly had significantly increased cell proliferation in comparison to vehicle controls with all three cell cycle markers. FIG. 14D reports the relative expression levels of TNFα in resected liver sections. TNFα is known to contribute to the restoration of functional liver mass through driving hepatocyte proliferation and liver regeneration. In summary, PPF1 treatment led to activation of cell proliferation in otherwise quiescent and intact livers (before hepatectomy) in comparison to vehicle control. Mean±SEM, *$p<0.05$ with Unpaired T test with Whitney correction.

FIG. 15 shows immunostaining of Ki67 in resected livers as reported in FIG. 14C, which confirms that PPF1-treated resected livers had significantly higher numbers of Ki67-positive cells in comparison to vehicle controls.

FIG. 16 reports quantification of immunostaining from FIG. 15, showing increased numbers of Ki67-positive cells in PPF1-treated resected livers. Mean±SEM, *$p<0.05$ with Unpaired T test with Whitney correction.

FIG. 17 is a chart showing the total number of animals that underwent hepatectomy as well as the survival rates for animals receiving each treatment. PPF1-treated animals exhibited a trend towards increased survival compared to vehicle-treated animals.

FIG. 18 displays two confocal microscopic fields from remnant liver incorporated with EdU 24 hours after hepatectomy (See FIG. 3). Histologic sections were stained with GFAP antibody (stellate cell marker) and levels of colocalization with EdU with GFAP observed. It was determined from the lack of colocalization between EdU and GFAP that cell proliferation associated with PPF1 administration did not occur in stellate cells.

FIG. 19 displays two confocal microscopic fields from remnant liver incorporated with EdU 24 hours after hepatectomy (See FIG. 3). The histologic sections were stained with CD68 antibody (Kupffer cell marker) and levels of colocalization with EdU with CD68 observed. It was determined from the lack of colocalization between EdU and CD68 that cell proliferation associated with PPF1 administration did not occur in Kupffer cells.

FIG. 20 displays a confocal microscopic field from remnant liver incorporated with EdU 24 hours after hepatectomy (See FIG. 3). The histologic section was stained with HNF4a antibody (hepatocyte cell marker) and levels of colocalization with EdU with HNF4a observed. It was determined from the lack of colocalization between EdU and HNF4a that cell proliferation associated with PPF1 administration did not occur in hepatocytes.

FIG. 21 displays a confocal microscopic field from remnant liver incorporated with EdU 24 hours after hepatectomy (See FIG. 3). The histologic section was stained with CD3 antibody (T-cell marker) and levels of colocalization with EdU with CD3 observed. It was determined from the lack of colocalization between EdU and CD3 that cell proliferation associated with PPF1 administration did not occur in T-cells.

FIG. 22 displays two confocal microscopic fields from remnant liver incorporated with EdU 24 hours after hepatectomy (See FIG. 3). The histologic sections were stained with CD31 antibody (sinusoidal endothelial cell marker) and levels of colocalization of EdU with CD31 observed. It was determined from a positive colocalization between EdU and CD31 that cell proliferation caused by PPF1 administration is associated with liver sinusoidal endothelial cells (LSECs). These results suggest that PPF1 increases capillary cell proliferation in liver which results in more blood brought to the injury site which suggests a mechanism of how tissue repair and regeneration occurs upon PPF1 treatment. (Arrows indicate LSECs that include EdU positive cells).

2. Example 2 a) Effects of PPF1, Recombinant Human Albumin, and HAS1 on 20-Month-Old C57BL/6 Mouse Livers After 70% Partial Hepatectomy Recombinant Human Albumin Male C57BL/6J were treated as described previously in Example 1 above, except an additional cohort was treated with recombinant human albumin ("rhAlbumin"). Comparisons between PPF1-treated, rhAlbumin-treated, and vehicle-treated groups were performed.

FIG. 23 shows the design of an experiment to evaluate effects of PPF1 (a type of plasma fraction "PF") and recombinant human albumin (rhAlbumin) on 20-month-old C57BL/6 mice on a high fat diet. The mice were placed on a 60% high fat diet for 8 weeks prior to treatment with PPF1, rhAlbumin, or vehicle for seven consecutive days. Surgery (70% hepatectomy) was performed the day after the last dose of PPF1, rhAlbumin, or vehicle, and pre-surgery median and left lobes (resected) were removed during the hepatectomy. The right and caudate lobes (remnant) were harvested 48 hours after hepatectomy.

FIG. 24 reports cell proliferation at 48 hours post-hepatectomy in resected livers as measured by the number of Ki67-positive cells per field. PPF1 significantly increased Ki67-positive number of cells per field compared to vehicle-treated animals. In contrast, rhAlbumin-treated animals exhibited no significant difference from vehicle-treated animals. Mean±SEM, ***$p<0.0001$ with Unpaired T test with Whitney correction, ns=not significant.

FIG. 25 reports cell proliferation rate after hepatectomy in remnant livers. EdU was delivered at 24-hours post-hepatectomy and the proliferation rates were traced by click-chemistry. PPF1 significantly increased the EdU-positive number of cells per field compared to vehicle-treated animals. In contrast, rhAlbumin-treated animals did not reach significance in proliferation compared to vehicle-treated animals.

These results reveal that albumin, which is the most abundant component of PPF1, is likely not the component of PPF1 responsible for its proliferative, tissue repair, and regenerative activity. It instead suggests that it is other components of PPF1, often considered impurities left over from plasma fractionation, that surprisingly drive these activities of PPF1.

Human Albumin Solution (HAS)

Male C57BL/6J were also treated as described previously in Example 1 above, except the additional cohort was treated with a human albumin solution ("HAS1"). Comparisons between PPF1-treated, HAS1-treated, and vehicle-treated groups were performed.

FIG. 26 shows the design of an experiment to evaluate effects of PPF1 and HAS1 on 20-month-old C57BL/6 mice on a high fat diet. The mice were placed on a 60% high fat diet for 8 weeks prior to treatment with PPF1, rhAlbumin, or vehicle for seven consecutive days. Surgery (70% hepatectomy) was performed the day after the last dose of PPF1, HAS1, or vehicle, and pre-surgery median and left lobes (resected) were removed during the hepatectomy. The right and caudate lobes (remnant) were harvested 48 hours after hepatectomy.

FIG. 27 reports cell proliferation rates 24 hours after hepatectomy. EdU was delivered at 24-hours post-hepatectomy. Both PPF1 and HAS1 significantly increased EdU-positive number of cells in comparison to vehicle in remnant livers. *$p<0.05$, Welch's t-test. Error bar=S.E.M. HAS1 is a commercially available HAS such as those Commercial HAS Preparations described above in 5% solution and were stored at 4° C.

FIG. 28 shows cell proliferation rates 48 hours after hepatectomy. Ki67 immunostaining was performed on remnant liver taken out 48 hours after hepatectomy. While both PPF1 and HAS significantly increased cellular proliferation in comparison to control animals, PPF1 also induced significantly more proliferation in comparison to HAS1-treated animals. *$p<0.05$, $p<0.005$, *$p<0.0005$ Welch's t-test. Error bar=S.E.M.

These results reveal that plasma fraction-induced liver cell proliferation was observed in both HAS1 and PPF1-treated steatotic livers. However, although both different plasma fractions (HAS1 and PPF1) significantly induced proliferation versus vehicle after 24 hours, the effect of PPF1 after 48 hours was considerably more significant compared to HAS1 and even more so compared to vehicle. This again indicates that albumin, which is purer and more abundant in HAS1 compared to PPF1, is surprisingly not the primary component responsible for the plasma fractions' effects on proliferation, tissue repair, and regeneration. Instead, it suggests that it is the other components of plasma fractions, or the "impurities" left over from plasma fractionation, that unexpected drive these activities.

3. Example 3 a) Effects of PPF1 on 20-Month-Old C57BL/6 Mouse Livers Two Hours After the Last Treatment Dose Twenty-month-old male C57BL/6J mice were randomized into vehicle versus PPF1 treatment groups according to their body weights to ensure the same average body weight between groups. The mice were raised on normal chow and not a high fat diet. I.V. daily dosing of 150 μL of vehicle or PPF1 was given to animals for 7 consecutive days. On the seventh day, the liver was removed 2 hours after dosing. For gene expression analysis, RNA was extracted and reverse transcribed and SYBR qPCR was performed for TNFα. Gene expression was normalized to RPS18. For immunostaining, Ki67 antibody was used to label proliferating cells in the harvested liver.

FIG. 29 shows the design of this experiment to evaluate the effects of PPF1 2 hours after last dose on 20-month-old C57BL/6 mice.

FIG. 30 shows results of TNFα gene expression analysis on mice treated as described in FIG. 29 above. In comparison to vehicle treated animals, PPF1 treated animals had a significant increase in TNFα gene expression by QPCR. **p<0.005. Welch's t-test, error bars=S.E.M.

FIG. 31 shows results of Ki67 immunostaining analysis on mice treated as described in FIG. 29 above. In comparison to vehicle treated animals, PPF1 treated animals at 2-hours after the last dose significantly increased Ki67-positive cells indicating an increase of liver cellular proliferation by PPF1. *p<0.05. Welch's t-test, error bars=S.E.M.

These results show that even in healthy, non-steatotic aged liver, plasma fractions such as PPF1 can be effective at inducing both proliferation and regeneration.

4. Example 4 a) Effects of Fraction IV-1 Paste Suspension on 20-Month-Old C57BL/6 Mouse Livers After 70% Partial Hepatectomy Male C57BL/6J mice (The Jackson Laboratory, Sacramento, Calif.) aged for 20 months are used. All mice are individually housed under specific pathogen-free conditions under a 12-hour light, 12-hour dark cycle, and all animal handling and use is in accordance with Institutional Animal Care and Use Committee approved standard guidelines. Animals are fed with 60% high fat diet (Bio-Serv F3282) for 7-8 weeks and randomized into vehicle vs Fraction IV-1 paste suspension treated groups according to their body weights and ALT levels after the diet to ensure the same average body weight and serum ALT levels between groups. Surgery is performed with minor modifications as described previously (Nevzorova, Y., et al., *Lab. Anim.* 49, 81-88 (2015)). The resected liver lobes (left and medial) are taken as pre-surgery controls whereas remnant liver lobes (caudal and right) are harvested 48 hour after surgery. Twenty-four (24) hours post-surgery, EdU (stock at 2.5 mg/mL in saline) is injected I.P. at 30 mg/kg of body weight. Forty-six (46) hours post-surgery, BrdU (stock at 10 mg/mL in saline) is injected I.P. at 30 mg/kg of body weight. At 48 h post-surgery, all animals are weighed, and remnant livers (medial and caudal) and serum are collected for ALT analysis. The effects of Fraction IV-1 paste suspension on these experimental readouts are compared to vehicle. Additionally, the effects of Fraction IV-1 paste suspension on these experimental readouts are compared to other plasma fractions.

The invention claimed is:

1. A method of inducing liver regeneration in a subject diagnosed with a liver disorder, the method comprising administering an effective amount of a Plasma Protein Fraction (PPF) to the subject, wherein the PPF comprises between 83% and 95% albumin in relation to total proteins.

2. The method of claim 1, wherein the administering is performed using a Pulse Dose dosing regimen.

3. The method of claim 1, wherein the liver disorder is acute liver failure.

4. The method of claim 1, wherein the liver disorder is chronic liver failure.

5. The method of claim 1, wherein the liver disorder is acute-on-chronic liver failure.

6. The method of claim 1, wherein the PPF is produced from blood plasma derived from humans 40 years of age or younger.

7. The method of claim 1, wherein the PPF comprises no more than 17% globulins and other plasma proteins.

8. The method of claim 1, wherein the PPF comprises no more than 1% gamma globulin.

* * * * *